(12) United States Patent
Flider et al.

(10) Patent No.: US 8,820,144 B2
(45) Date of Patent: Sep. 2, 2014

(54) APPARATUS AND METHOD FOR FLUID MONITORING

(75) Inventors: Gennadiy Flider, San Francisco, CA (US); Gabreal Livschits, San Francisco, CA (US)

(73) Assignee: International Environmental Technologies, Inc., San Francisco, CA (US)

( * ) Notice: Subject to any disclaimer, the term of this patent is extended or adjusted under 35 U.S.C. 154(b) by 433 days.

(21) Appl. No.: 13/154,280

(22) Filed: Jun. 6, 2011

(65) Prior Publication Data

US 2012/0029845 A1   Feb. 2, 2012

Related U.S. Application Data

(60) Provisional application No. 61/351,913, filed on Jun. 6, 2010, provisional application No. 61/370,799, filed on Aug. 4, 2010.

(51) Int. Cl.
  *G01F 1/56*   (2006.01)
  *G01N 27/74*   (2006.01)
(52) U.S. Cl.
  CPC ..................................... *G01N 27/74* (2013.01)
  USPC ....................................................... 73/53.01

(58) Field of Classification Search
  USPC ......................................................... 73/53.01
  See application file for complete search history.

(56) References Cited

U.S. PATENT DOCUMENTS

| | | | |
|---|---|---|---|
| 4,067,216 A * | 1/1978 | Khimenko et al. | ................ 72/56 |
| 6,188,151 B1 * | 2/2001 | Livshits et al. | ................. 310/30 |
| 6,320,393 B1 * | 11/2001 | Yasui et al. | ..................... 324/663 |
| 7,121,158 B2 | 10/2006 | Scott et al. | |
| 7,143,638 B1 * | 12/2006 | Scott | ............................ 73/61.43 |
| 7,193,414 B2 | 3/2007 | Kruspe et al. | |
| 7,270,784 B2 | 9/2007 | Vuong et al. | |
| 7,690,391 B2 | 4/2010 | Guest et al. | |
| 7,725,272 B2 | 5/2010 | Ginggen et al. | |
| 2002/0151816 A1 * | 10/2002 | Rich et al. | ..................... 600/547 |
| 2010/0045309 A1 * | 2/2010 | Zou et al. | ...................... 324/663 |

* cited by examiner

*Primary Examiner* — Hezron E Williams
*Assistant Examiner* — Mark A Shabman
(74) *Attorney, Agent, or Firm* — Knobbe, Martens, Olson & Bear LLP

(57) ABSTRACT

According to some embodiments, an apparatus and method are provided for detecting the composition of a fluid. An alternating electromagnetic field may be applied to the fluid and distortions in the electromagnetic field are compared with predetermined, expected distortion "signatures" for particular components at particular concentrations. The presence and concentration of the components in the fluid may be detected by detecting these distortion signatures.

10 Claims, 24 Drawing Sheets

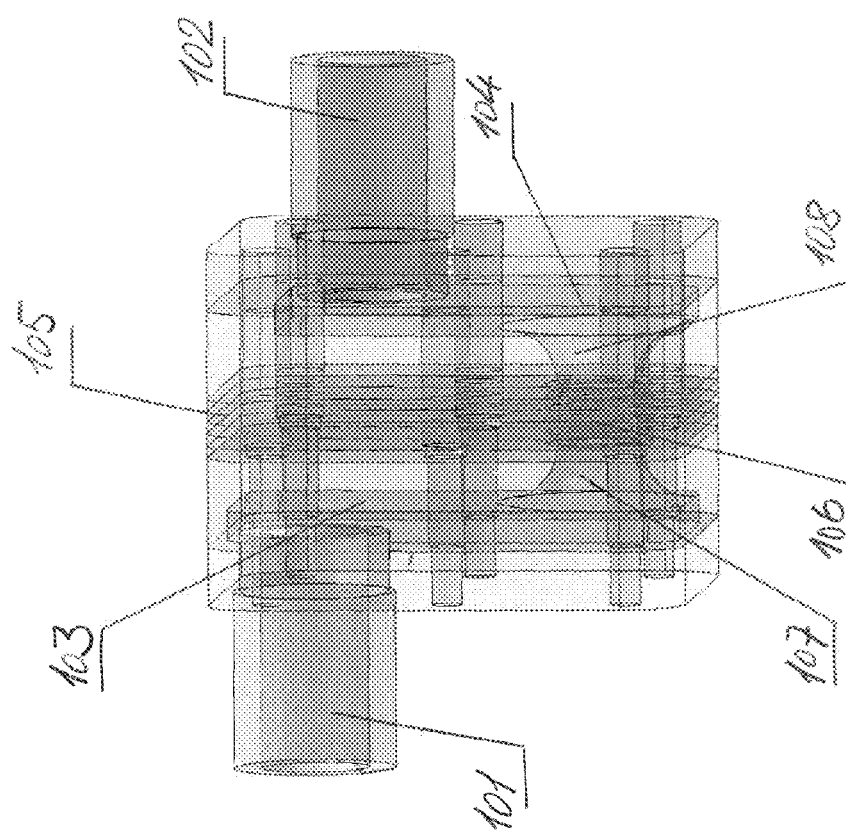
Fig. 1

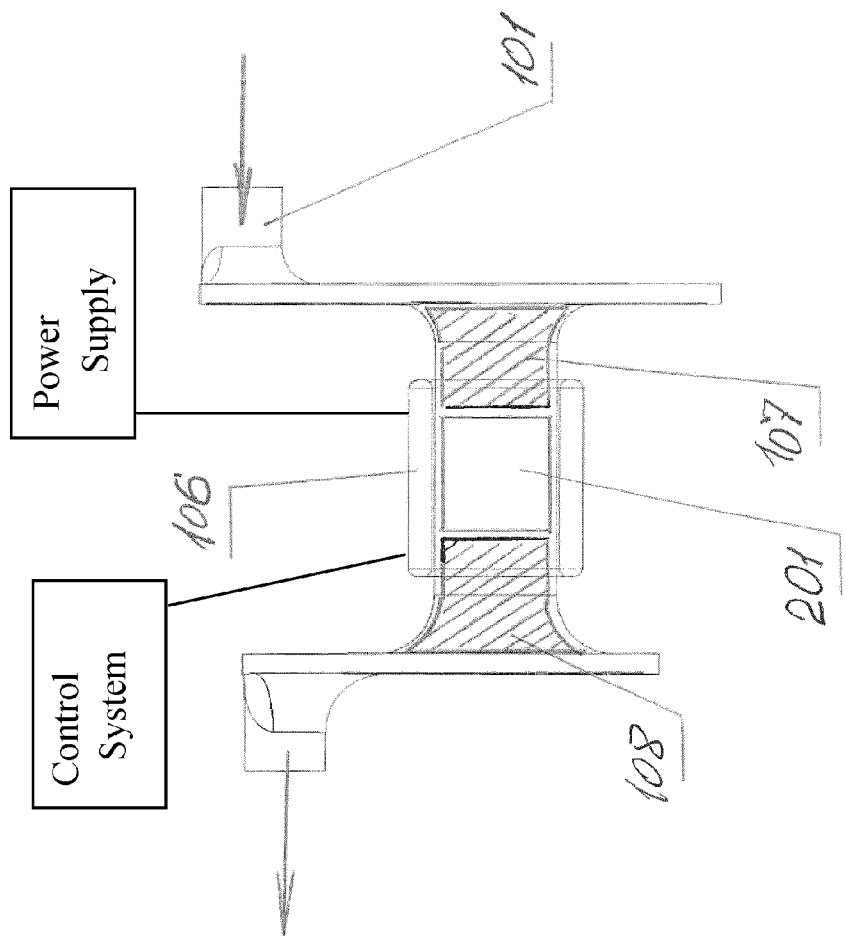

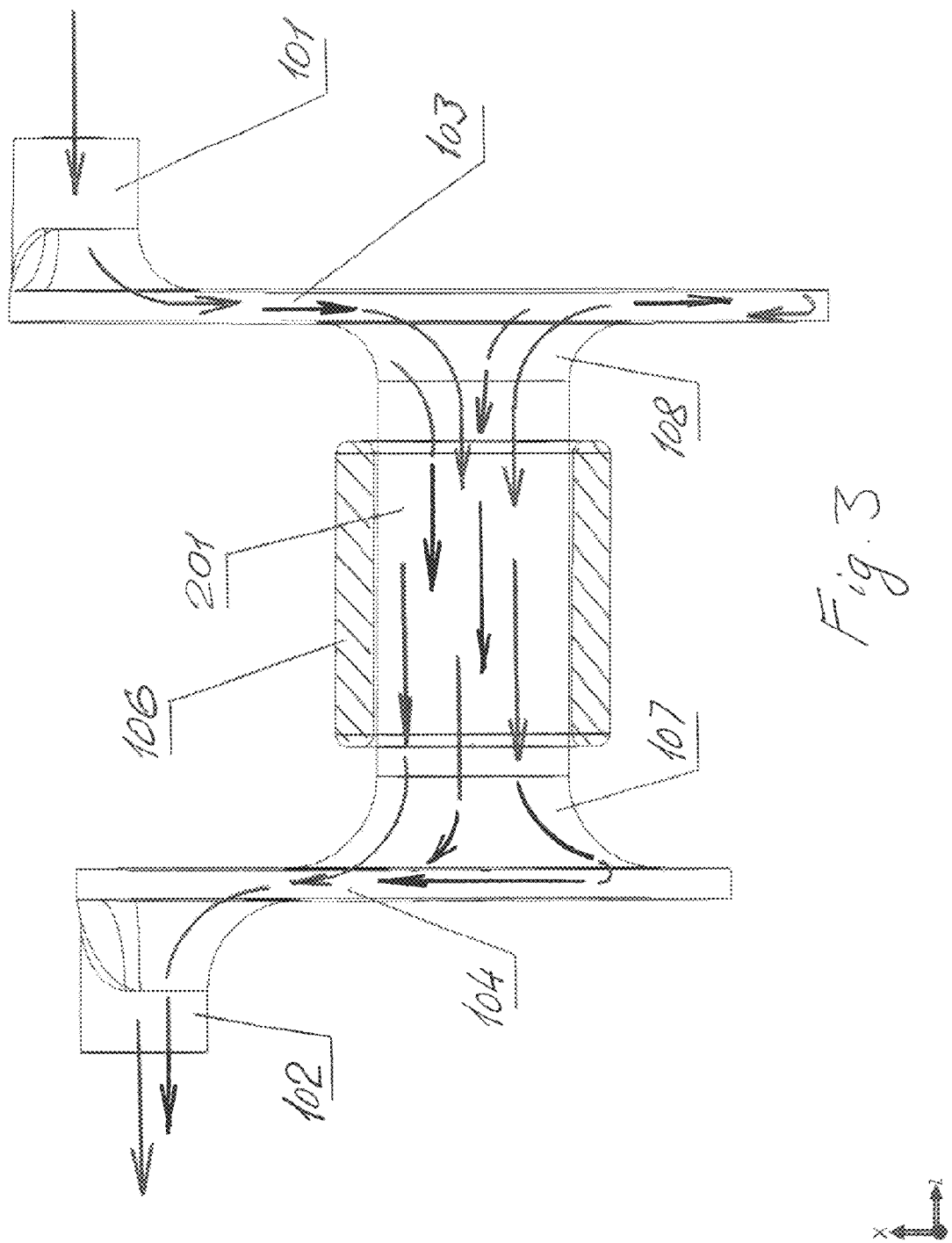

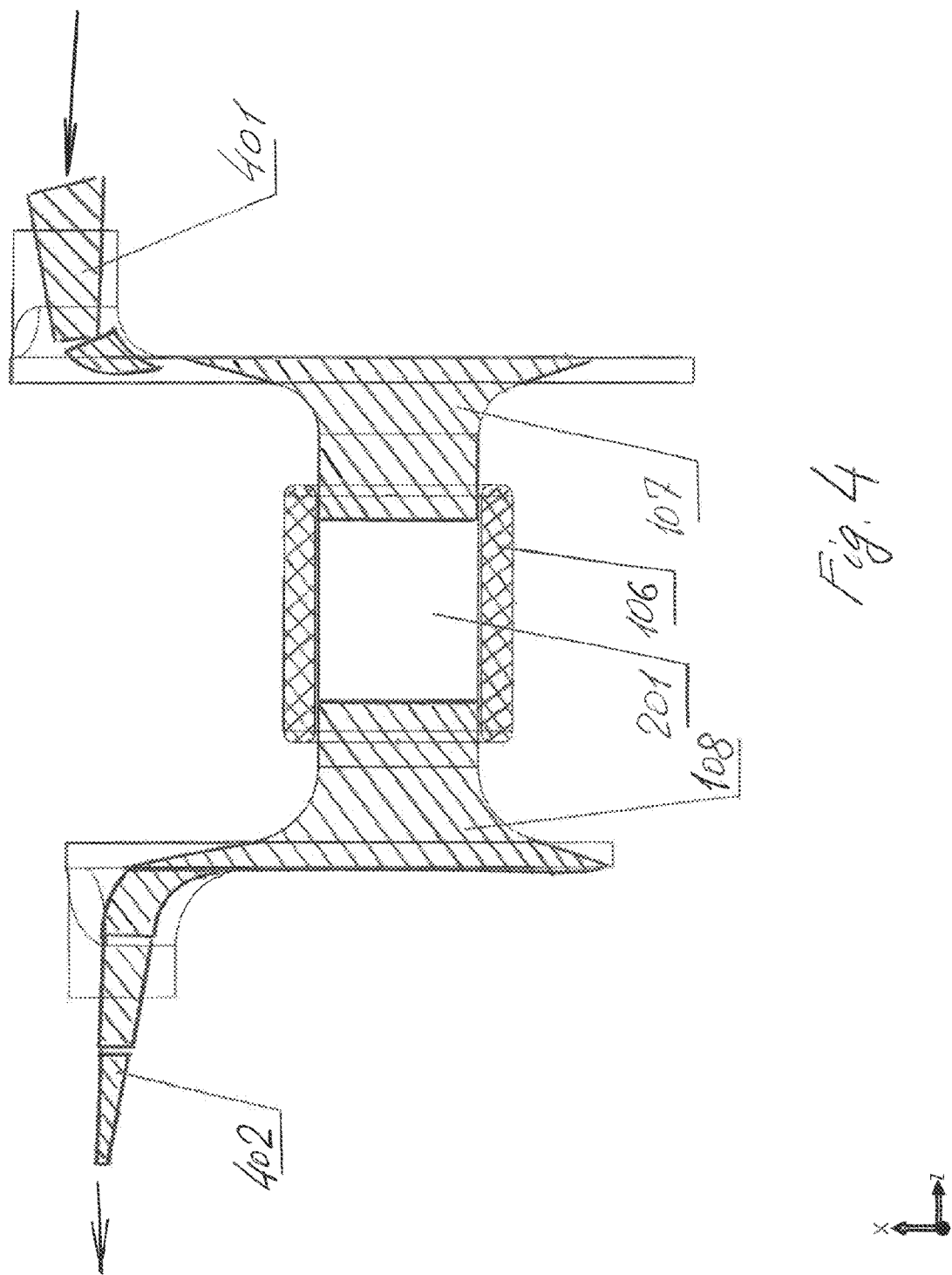

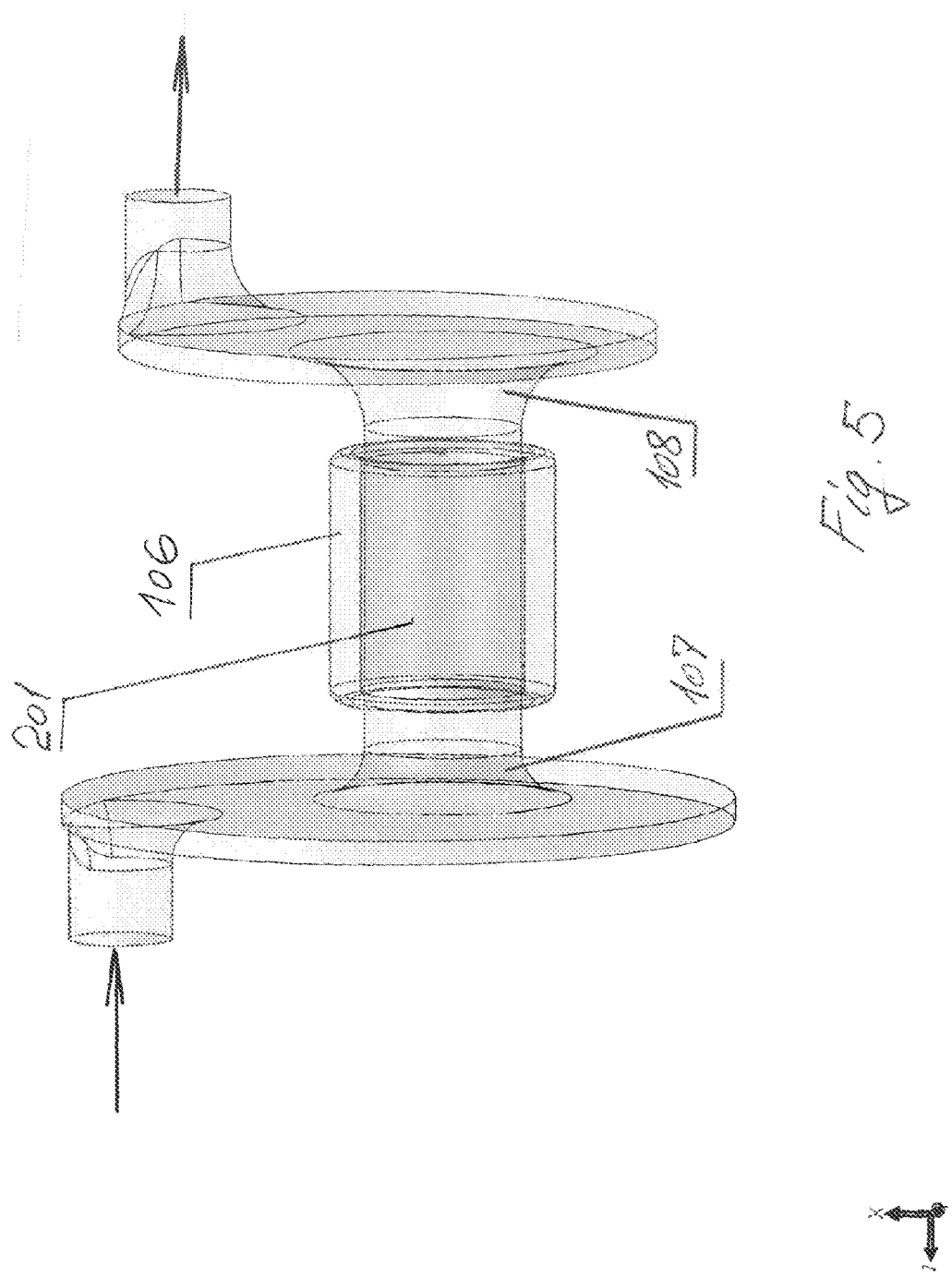

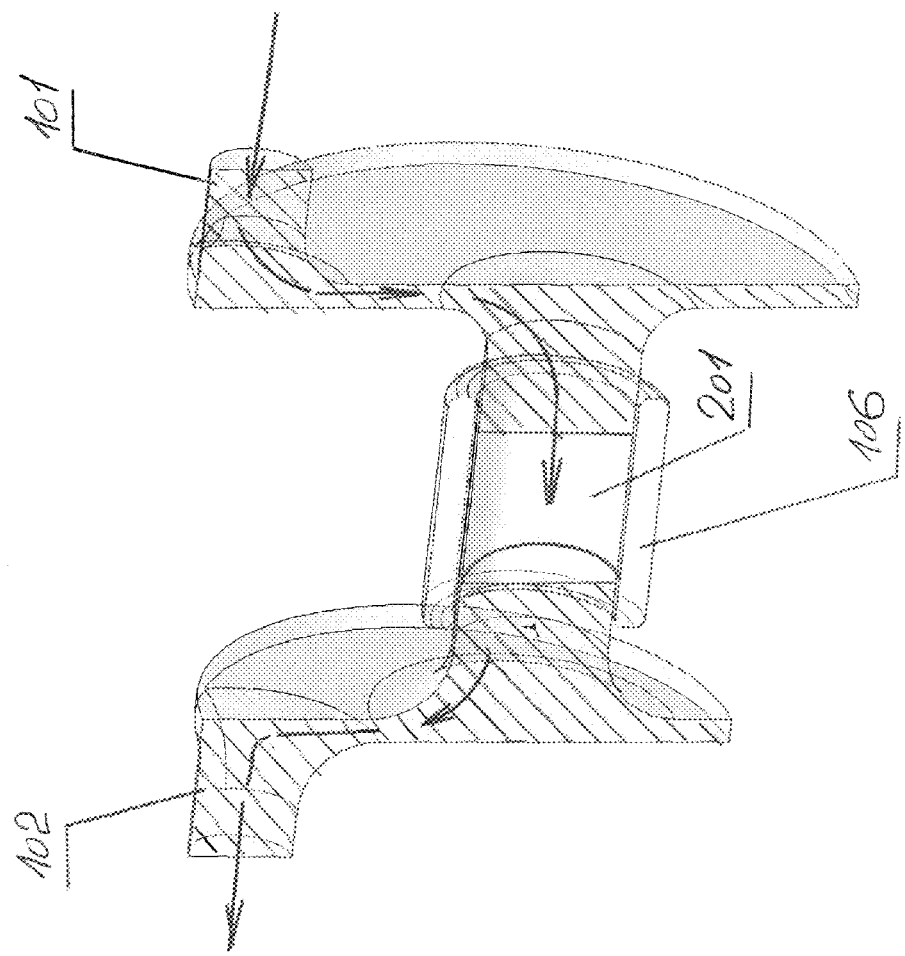

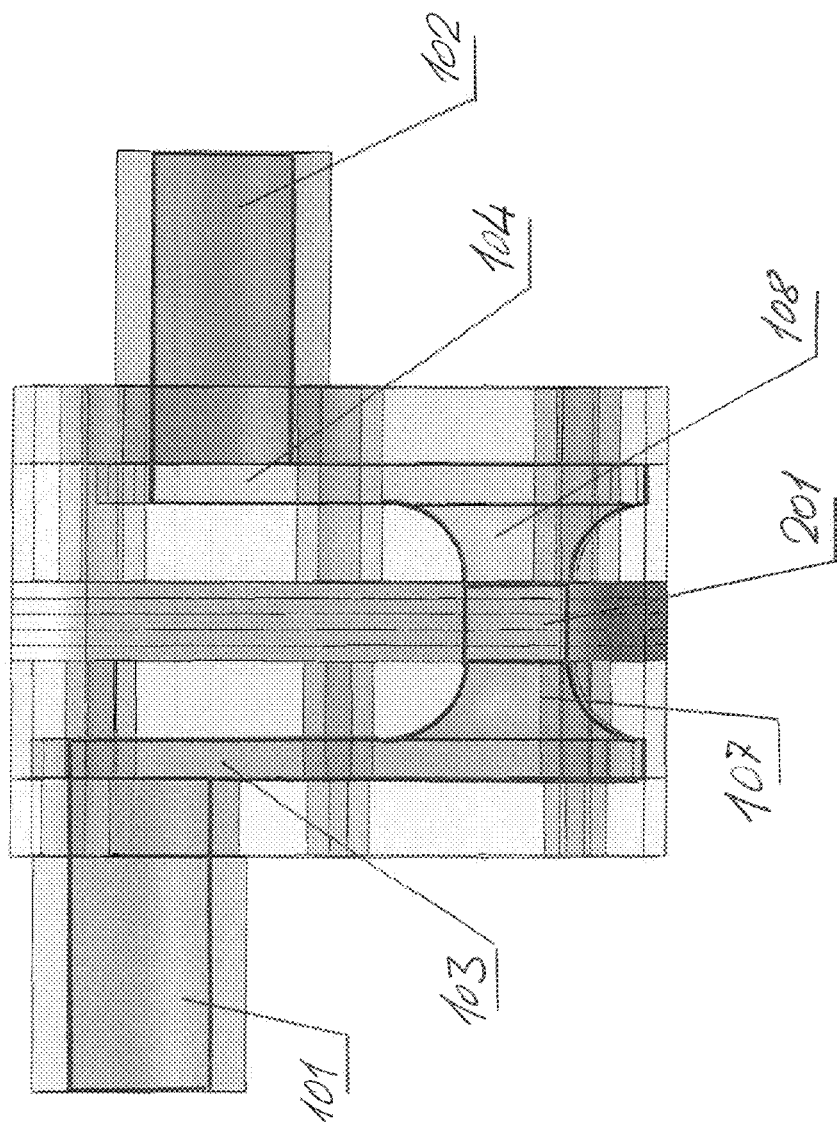

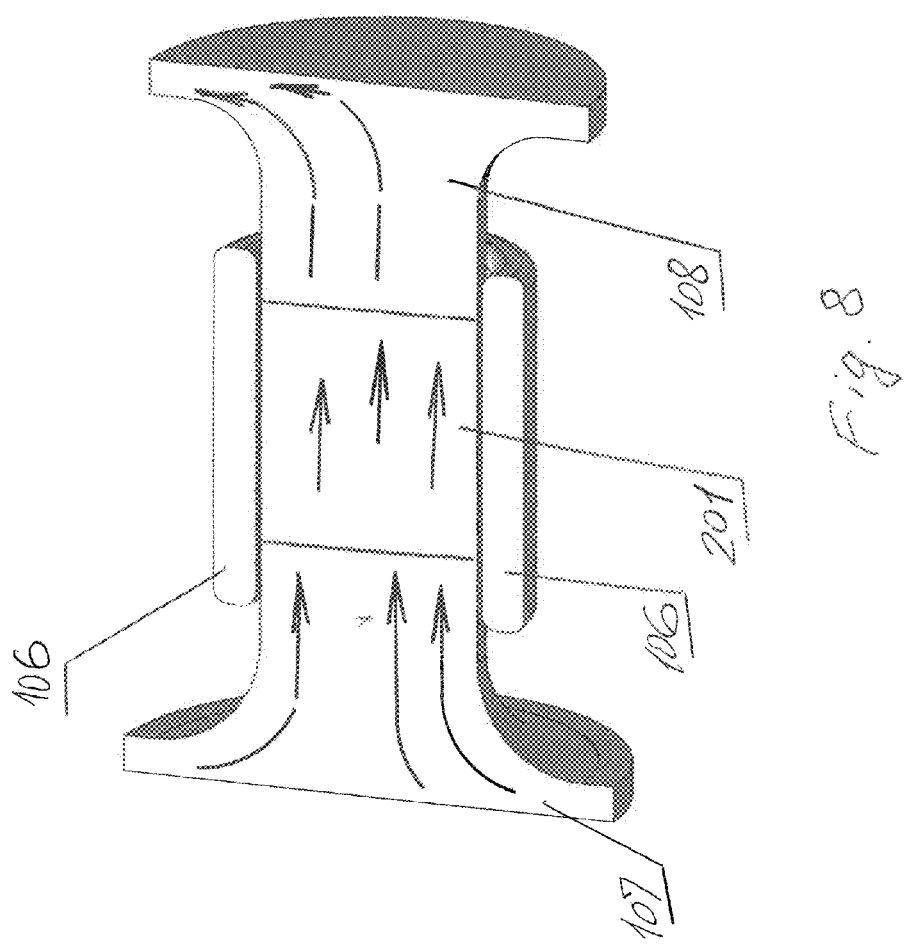

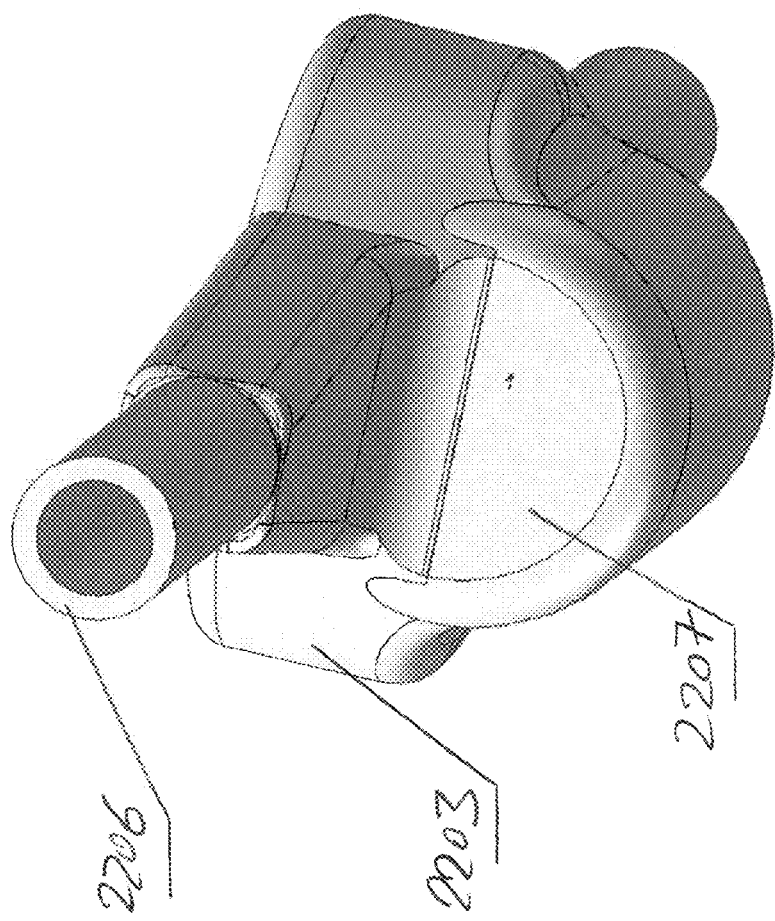

APPARATUS AND METHOD FOR FLUID MONITORING

REFERENCE TO RELATED APPLICATIONS

This application claims the priority benefit under 35 U.S.C. §119(e) of U.S. Provisional Application No. 61/351,913, filed Jun. 6, 2010; and 61/370,799, filed Aug. 4, 2010. The entire disclosures of each of these applications are incorporated herein by reference.

TECHNICAL FIELD

The invention relates to apparatus and methods for monitoring fluids by application of an electromagnetic field to the fluids. For example, the composition of the fluids may be determined.

DESCRIPTION OF THE RELATED TECHNOLOGY

Various technologies for monitoring linear dimensions are used in different industries. Various technologies are also used for monitoring and measuring the parameters and concentrations of various fluids and solutions. In many cases, such measurements and monitoring are very difficult under conditions where the monitored volume is in a turbulent state. For example, this difficulty applies to fluids and solutions transported along pipelines and which may experience high pressure and movement at high speeds. The pressure or movement can create high turbulence levels along the course of the fluid or solution's movement along the pipeline or a hydraulic pipe, which in turn affects the precision of measuring and monitoring instruments and devices.

Monitoring fluids involves certain conditions and aspects, which are not characteristic of solids. For example, these conditions and parameters include non-constant values for electrical conductivity, acidity and alkalinity as well as potential surges in the quantity and composition of substances dissolved or otherwise contained in the fluid. Changes in any of the above parameters may introduce a significant error into the process involved in monitoring fluid parameters and measuring or monitoring the concentration of these dissolved substances. Changes in fluid flow turbulence in combination with changes in these factors above can also introduce errors. Accordingly, there is a need for an apparatus and method for accurately measuring the composition or properties of a fluid.

SUMMARY

According to some embodiments of the invention, remote and non-contact monitoring of the state of an object as a whole, and the proportions and parameters of the state of the components of that object, for multi-component objects, are facilitated. Both direct and indirect measurements may be used. The monitoring may be applied to various industries, including agriculture and medicine. In some embodiments, the fluid flow rate in a pipeline may be determined while simultaneously monitoring its chemical composition. The fluid monitoring can allow continuous determination of chemical composition, e.g., in a moving fluid stream such as drinking water in a piping system.

In some embodiments, programs, systems and methods of dynamic fluids content monitoring are provided. The following steps may be performed to determine the composition of a fluid:

define a constant for the characteristic of a solenoid by a measuring contour of the device for monitoring structure and concentration of the components of a liquid, at constants to frequency of the impulse submitted on the solenoid and the quantity of coils of the solenoid;

compare the received constant of the characteristic of the solenoid with the average statistical value of the specified constant of the characteristic of the solenoid, at constants to frequency of the impulse submitted on the solenoid and quantity of coils of the solenoid;

at positive results for the comparison, define a size of a controllable parameter of structure and concentration of components in a liquid having counting upon about, e.g., one millivolt of amplitude of measurement; and calculate a measured parameter, by multiplication of size of a controllable parameter of structure and concentration of components of the liquid having counting upon about, e.g., one millivolt of amplitude of measurement on the measured size of amplitude.

In some embodiments, further programs, systems and methods for dynamic fluids content monitoring are provided, where the definition of a constant for the characteristic of the solenoid for a measuring contour of the device for monitoring structure and concentration of components of a liquid, at constants to frequency of the impulse submitted on the solenoid and quantity of coils of the solenoid, is carried out with the following relationships:

$$P_1 = M/A,$$

where:

$P_1$=size of a controllable parameter of structure and concentration of components of the liquid having counting upon about, e.g., one millivolt of amplitude of measurement;

M=average statistical size of a measured parameter at equal values of frequency of a signal submitted on the solenoid and quantity of coils of the solenoid of an oscillatory measuring contour of the device; and A=the measured size of amplitude, at equal value of frequency of the signal submitted on the solenoid of an oscillatory measuring contour of the device and quantity of coils of the solenoid.

$$P_1/M = K,$$

where:

K=a constant of the characteristic of the solenoid of a measuring contour of the device for monitoring structure and concentration of components of a liquid, at constants to frequency of the impulses submitted on the solenoid and quantity of coils of the solenoid.

After mathematical transformations, the relationship becomes:

$$K = M/A/M = 1/A$$

Also in some further embodiments, programs, systems and methods of dynamic fluids content monitoring are also provided. Calculation of a measured parameter, by multiplication of the size of a controllable parameter of structure and concentration of components of the liquid having counting upon about, e.g., one millivolt of amplitude of measurement on the measured size of amplitude, is carried out with the following relationships:

$$P_1 \times A = M,$$

where:
- $P_1$=the size of a controllable parameter of structure and concentration of components of the liquid having counting upon about, e.g., one millivolt of amplitude of measurement;
- A=the measured size of amplitude, at equal value of frequency of the signal submitted on the solenoid of an oscillatory measuring contour of the device and quantity of coils of the solenoid; and
- M=the size of a measured parameter at equal values of frequency of a signal submitted on the solenoid and quantity of coils of the solenoid of an oscillatory measuring contour of the device.

In some embodiments, an apparatus is provided with ducts for the passage of monitored fluids. The ducts are built in such a way that the fluid is inside a solenoid cavity, which has at its inlet and outlet a shape for forming a core as part of the magnetic conductor of the monitoring module.

Conical reflectors at the inlet and outlet of the solenoid represented by a coil in a pulsed electromagnet in the monitoring module, ensure a high magnetic field insulation, and prevent the loss of field energy thus enhancing the energy saturation of the signal sent to the monitored fluid, and increasing the energy saturation of the resonance in response to the signal sent to the monitored fluid. This effect significantly increases monitoring precision and makes it possible to selectively isolate resonance at a frequency characteristic of the specific substance contained in the monitored fluid.

In some embodiments, an apparatus for dynamic fluid monitoring comprises a monitoring module connected to the system for monitored fluid flow turbulence level transformation and transformed fluid flow inflow into the monitoring module, and to the system for fluid flow turbulence level restoration and fluid flow outflow from the monitoring module, in which the monitored fluid flow is connected to the RLC (resistor, inductor, capacitor) circuit feed element of the monitoring module as a core with a pulsed electromagnet.

In some other embodiments, an apparatus is provided with a system for monitored fluid flow turbulence level transformation and the transformed flow inflow into the monitoring module, a monitoring module hydraulic system and a system for monitored fluid flow turbulence level restoration and fluid flow outflow from the monitoring module as communicating vessels which includes communicating vessels.

In some other embodiments, an apparatus is provided with a system for monitored fluid flow turbulence level transformation and the transformed flow inflow into the monitoring module, a monitoring module hydraulic system and a system for monitored fluid flow turbulence level restoration and fluid flow outflow from the monitoring module as communicating vessels which includes two vertical components and one horizontal component connecting them.

In some embodiments of the various apparatus, the first vertical component of the communicating vessels serves as a system for monitored fluid flow turbulence level transformation and the fluid flow inflow into the monitoring module, and the second one as the system for monitored fluid flow turbulence level restoration and fluid flow outflow from the monitoring module having an RLC circuit feed element installed coaxially to the horizontal component of the communicating vessels, whereas the monitored fluid flow in the horizontal component is connected to the feed element as a core with a pulsed electromagnet.

The feed element may be a solenoid connected to the power supply and control systems. To this end, the system for monitored fluid flow turbulence level transformation and the fluid transformed flow inflow into the monitoring module may have a conical reflector, coaxial to the RLC circuit feed element of the monitoring module with cone peak pointed toward monitoring module inlet.

The system for monitored fluid flow turbulence level restoration and the fluid flow outflow from the monitoring module may have a conical reflector coaxial to the RLC circuit feed element of the monitoring module with cone peak pointing toward monitoring module outlet.

Structurally, the apparatus can be provided with a conical reflector coaxial to the RLC circuit feed element of the monitoring module with cone peak pointing toward monitoring module inlet and a conical reflector coaxial to the RLC circuit feed element of the monitoring module with cone peak pointing toward monitoring module outlet, in conjunction with communicating vessel horizontal component disposed in the RLC circuit feed element of the monitoring module are components forming the dynamic core of the pulsed electromagnet.

In the apparatus, the system for monitored fluid flow turbulence level transformation and the transformed fluid flow inflow into the monitoring module, a monitoring module hydraulic system and a system for monitored fluid flow turbulence level restoration and fluid flow outflow from the monitoring module can represent communicating vessels comprised of two vertical components, and one horizontal component connecting them and having at least one duct predominantly cylindrically shaped.

The apparatus can also comprise a system for monitored fluid current turbulence level transformation and the fluid transformed flow inflow into at least one monitoring module, a hydraulic system of at least one monitoring module, and a system for monitored fluid flow turbulence level transformation and fluid flow outflow from at least one monitoring module representing communicating vessels comprising two vertical components, and one horizontal component connecting them and having at least one duct predominantly cylindrically shaped and at least one solenoid acting as RLC circuit feed element of the monitoring module disposed coaxially to the duct.

In some embodiments, the method of operation of the device involves generating an alternating electromagnetic field in the horizontal duct of the monitoring module in which the monitored or investigated sample is disposed or in which the monitored fluid flows. The field acts as a sort of an intermediary between the LC circuit and the fluid. The LC circuit, owing to the presence of the feed element, is an emitter (transmitter) of the field, on the one hand, and, on the other hand, a receiver (a sensing element) of the electromagnetic field changes caused by the tested (monitored) sample—e.g., the fluid flowing in the horizontal duct of the monitoring module. The fluid flow is characterized by impedance, which is the parameter that is measured, identified and analyzed. Active and inductive resistance, as well as capacitive reactance, represent the component parts of impedance as the parameter measured according to the proposed method.

An external alternating electromagnetic field in the fluid causes electrical phenomena such as eddy currents, displacement currents (caused by dielectric polarization) and orderly ion movement (ion currents) to be induced under the impact of the external alternating electromagnetic field in the fluid. The field superposition principle indicates that these electrical phenomena distort the external alternating electro-magnetic field. These distortions are sensed by the solenoid which forms the electro-magnetic field and which is part of the monitoring module, while the LC circuit as a whole which contains this solenoid, senses these distortions as additional elements—condenser, inductance coil and resistor. The change of LC circuit parameters is reflected in the parameters of its amplitude frequency characteristics which in turn changes the resonance frequency and amplitude of the circuit. These changes make it possible to assess the component and integrated parameters of impedance of the monitored fluid and to compare impedance parameters of the flowing fluid with the statistical model of these parameters and their combinations, as well as the parameters of the tested or monitored fluid material object.

The following can be provided to facilitate monitoring:
- form a three-dimensional space system in which the feed and monitoring component, the solenoid, encircles the controlled element, the fluid;
- combine cross section centers of symmetry of the monitoring and monitored components of the three-dimensional space system;
- stabilize a uniform gap between the external surface of the monitored component and the internal surface of the monitoring component of the three-dimensional space system;
- around and inside the volume occupied by the monitoring component, form an energy saturated space represented by an alternating electromagnetic field with intensity monitored and controlled;
- ensure that the alternating electromagnetic field affects the monitored component and induces in it eddy currents, displacement currents and orderly ion movement in the form of ion currents, with displacement currents forming by dielectric polarization;
- identify and perform a comparative analysis of the distortions arising in the alternating electromagnetic field and ensure that monitoring component's LC circuit senses them as additional components—condenser, inductance coil and resistor; and
- register the levels of the distortions and changes occurring in amplitude and frequency characteristics of the LC circuit parameters, and use them to assess the monitored component impedance which defines the parameters of the state of the fluid material object.

In some embodiments, the energy-saturated space is an electromagnetic field having two components—magnetic and electric; the primary characteristics of a magnetic field is magnetic flow density or magnetic induction. An electric field is defined by intensity, a parameter, which, by endowing the monitored fluid with properties and functions of a magnetic conductor core formed by monitoring module components, creates a system which can be monitored and controlled to allow the desired precision and flexibility of measurements and monitoring of the various parameters of fluid material objects.

BRIEF DESCRIPTION OF THE DRAWINGS

The invention will be better understood from the Detailed Description and from the appended drawings, which are meant to illustrate and not to limit the invention. The Figures are not necessarily drawn to scale, nor are the relative sizes of parts within the Figures necessary in proportional to one another.

FIG. 1 is an example of a three-dimensional model of an apparatus according to embodiments of the invention.

FIG. 2 is an example of a diagram of the communicating vessels in the hydraulic system of an apparatus according to embodiments of the invention.

FIG. 3 shows an example of communicating vessels in the hydraulic system of an apparatus according to embodiments of the invention, with arrows indicating fluid flow movement directions in an apparatus according to embodiments of the invention.

FIG. 4 shows an example of components of the dynamic magnetic conductor of a monitoring module RLC circuit.

FIG. 5 shows an example of a three-dimensional model of the communicating vessels in an apparatus according to embodiments of the invention.

FIG. 6 is a cross-section view of the three-dimensional model of the communicating vessels in an apparatus according to embodiments of the invention.

FIG. 7 shows an example of a flat model of the section of the communicating vessels of the apparatus, identifying monitored fluid flow components, which form the dynamic core of the monitoring module RLC circuit, in which the RLC circuit can function as an equivalent of a pulsed electromagnet.

FIG. 8 is an example of a longitudinal section of the model of the core of an equivalent of a pulsed electromagnet of the monitoring module of an apparatus according to embodiments of the invention.

FIG. 24 is an example of a three-dimensional module of the fluid flow rate counter with a built-in an apparatus according to embodiments of the invention for monitoring fluid component concentration.

DETAILED DESCRIPTION

Figure 9:
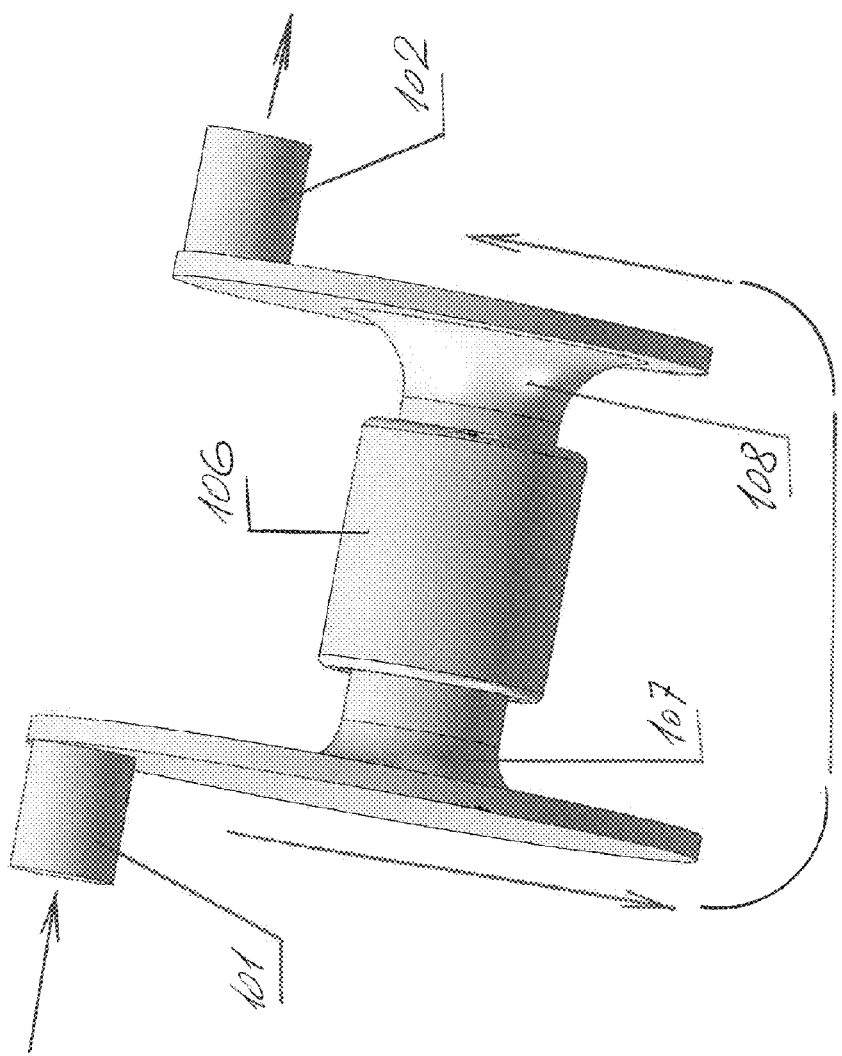
FIG. 9 is an example of a three-dimensional model of the communicating vessels of an apparatus according to embodiments of the invention.

According to some embodiments, an apparatus and system are provided for detecting the composition of a fluid. An alternating electromagnetic field may be applied to the fluid and distortions in the electromagnetic field are compared with predetermined, expected distortion "signatures" for particular, expected components. Advantageously, the presence and concentration of the components in the fluid may be detected by detecting these distortion signatures.

In some embodiments, a solenoid has an interior volume, into which a fluid to be monitored may be disposed. The fluid has a particular component or parameter to be monitored. This component or parameter can be measured by detecting the interaction of the component or parameter with the electromagnetic field generated by a solenoid. Energy of a particular amplitude is supplied to the solenoid, thereby causing the solenoid to generate an electromagnetic field of a particular frequency. The impedance of the fluid in the solenoid is measured and is different from a reference fluid that does not have the component or parameter. In addition, the impedance measurement is compared against a table of values for that particular solenoid, at the particular amplitude and frequency and with the particular type of fluid which is being measured. The measured impedance is matched with a value in the reference table, which is derived from the measurement of various known samples that have known compositions and concentrations. Thus, the table correlates particular measured impedances with particular concentrations of a fluid component, or with particular magnitudes for a particular parameter, e.g., acidity or alkalinity. By matching the measured impedance with impedance values on the table, the impedance measurement can be "interpreted"; for example, a particular measurement indicates a particular component at a particular concentration.

In order to develop a table correlating impedance values, known reference samples are first measured using different solenoids. The number of solenoids used and the types and numbers of reference samples used can vary depending upon the type of fluid monitoring that is desired. In some embodiments, a fluid is tested for one or more components that may be dissolved or suspended in the fluid.

To develop a reference table, multiple solenoids that generate different electromagnetic fields are tested in conjunction with different reference samples. For example, the references samples can be a solution having a known component at varying concentrations. In addition, it will be appreciated that the frequency of the electromagnetic field generated by a solenoid may depend, e.g., on the number of coils in the solenoid (the number of windings), the size of the solenoid (e.g., the diameter of the coils), and the thickness of the conductor forming the individual coils. The reference solutions may vary from being a pure liquid (e.g., distilled water) or solvent for the particular component to be measured, to a solution or mixture with a high concentration of the component. Each reference solution is provided in or loaded into different solenoids (different in number of coils, sizes, and/or conductor thicknesses) that produce different electromagnetic fields. In addition, the amplitude of the energy supplied to the solenoid may be varied (e.g., by 1 mv increments). In all cases, the impedance of the solution or mixture is measured. Thus, for every type of solenoid and every amplitude tested, a particular measured impedance is correlated with a particular concentration of the component being tested for.

It will be appreciated that some solenoid configurations result in a stronger signal-to-noise ratio, or otherwise are correlated more strongly with a particular component, in comparison to other components. In some embodiments, once the reference table has been established, the solenoid that gives the highest signal-to-noise ratio, or strongest correlation, is used in the field (e.g., at a testing site) to measure an unknown sample. In order to determine which solenoid or amplitude gives the highest signal-to-noise ratio, or strongest correlation, reference samples that contain components, other than the component being tested for, but which are expected to be in a solution or mixture, are also measured and provided in the table. Particular solenoid configurations that correlate to components other than or in addition to the component of interest are deemed to have high noise. Solenoid configurations that give an impedance measurement that correlates strongly with only the component of interest will typically be the configuration employed in the field. In some cases, a single solenoid may provide a high signal-to-noise ratio, or strong correlation with multiple components or parameters to be measured. In such cases, that single solenoid may be used to measure those multiple components or parameters in unknown samples. In other cases, more than one solenoid may be employed to monitor a particular sample, if the components or parameters to be measured require different solenoids to provide the desired high signal-to-noise ratio, or strong correlation. For example, different solenoids may be used to test for different components; or a single component may be tested for with two or more solenoids, where a single solenoid does not provide sufficient signal-to-noise, but two or more solenoids generate different types of noise, while providing a good signal for the component to be tested, so that a high correlation can be established using the impedance measurements from these two or more solenoids.

In some embodiments, the impedance measurement of a sample is compared to the reference impedance found in a reference sample without any or the component that is being monitored. An impedance measurement that is the same as the reference impedance indicates that the component is not present in a sample, while a difference indicates the presence of the component, with the degree of the difference indicating the amount of the component present.

It will be appreciated that the reference table may be resident in a computer, e.g., in the memory of a computer system. The computer system may have a processor that is configured or programmed to receive impedance measurements from a sample and to match those measurements with values in the reference table. Where an exact match cannot be found, e.g., where the measured impedance is between two table values, an interpolation can be performed to derive an intermediate value corresponding to the measured impedance. Thus, the presence and concentration of a component in a fluid may be determined.

In some embodiments, the apparatus has a three-dimensional structure where the measuring element encircles the measured element, and where the measured and monitored element is predominantly a fluid. The apparatus may be standalone and its work cycle may not depend on and is not connected to the equipment in which or for which the monitoring is being performed. In some other embodiments, the apparatus has a three-dimensional structure and is built into the equipment and its operation depends on and is tied to the functionality of the primary equipment.

In some embodiments, an apparatus for dynamic fluids control includes a monitoring module connected to the system for monitored fluid flow turbulence level transformation and transformed fluid flow inflow into a monitoring module, and with a system for monitored fluid flow turbulence level restoration and fluid flow outflow from the monitoring module in which the monitored fluid flow is connected with RLC circuit feed element of the monitoring module as a core with a pulsed electromagnet. Ducts for monitored fluid passage are built in such a way that the fluid inside the solenoid cavity, at its inlet and outlet, has a shape for forming a core as part of the magnetic conductor of the monitoring module. Conical reflectors at solenoid inlet and outlet, which in the controlled module is represented by the coil of a pulsed electrical magnet, amplify magnetic field insulation and preclude field power loss, thus increasing the energy saturation of the signal transmitted to the monitored fluid and correspondingly increasing resonance power saturation at the signal transmitted to the monitored fluid.

Reference will now be made to the figures, in which like numerals refer to like parts throughout.

In FIG. 1 of an example of a three-dimensional model of an apparatus according to embodiments of the invention is illustrated. The apparatus may be configured for performing dynamic measurements and monitoring of the composition of various substances dissolved in fluids. The following reference numerals identify the following features:

101—A pipeline through which fluid enters the apparatus.
102—A pipeline through which the fluid exits the apparatus.
103—The vertical duct where the first branch of the apparatus hydraulic system communicating vessels forms. In the vertical duct, fluid flow turbulence level transformation and decrease occurs, or turbulent fluid flow becomes laminar.
104—The vertical duct where the second branch of the apparatus hydraulic system communicating vessels forms. In the vertical duct, fluid flow turbulence level transformation and return of the level to fully developed turbulent state occurs, or turbulent fluid flow becomes laminar.
105—A multi-layer printing circuit board.
106—A solenoid of the apparatus' monitoring module with a horizontal segment connecting vertical branches of communicating vessels disposed along its axis.
107—A conical reflector with a peak pointing toward solenoid 106 duct inlet, which is a part of the magnetic conductor and the RLC circuit, and the base of liquid dynamic core of the magnetic conductor of a type of pulsed electrical magnet included in the monitoring module RLC circuit.
108—A conical reflector with peak pointing toward solenoid 106 duct outlet, which is a part of the magnetic conductor and the RLC circuit, and the peak of liquid dynamic core of the magnetic conductor of a type of pulsed electrical magnet included in the monitoring module RLC circuit.

Apparatus structural components 107, 106 and 108 may form the dynamic core of the electromagnetic RLC system as part of the active magnetic conductor of the system, in which due to the presence of this core and its shape, magnetic field energy losses significantly decrease and energy saturation increases by an order of magnitude.

FIG. 2 shows an example of a three-dimensional model of ducts forming a system of communicating in an apparatus according to embodiments of the invention. In the system, the horizontal segment is the dynamic core of the pulsed electromagnet formed by the solenoid 106 and the components of the dynamic magnetic conductor 107 И 108. Number 201 in the figure designates a segment of the fluid flow which is the object for measurement or monitoring and is disposed directly in the solenoid duct.

FIG. 3 shows a fluid flow model during its passage inside the communicating vessels of the hydraulic system of the apparatus and its monitoring module.

FIG. 4 shows a model of the magnetic field distribution in the monitored fluid dynamic flow during its passage in the hydraulic system of the apparatus. The following reference numerals identify the following features:

401-Potential leaks of magnetic lines of force of the magnetic field into the fluid inflow pipeline of the apparatus.
402-Potential leaks of magnetic lines of force of the magnetic field into the fluid outflow pipeline of the apparatus.

FIG. 5 shows a three-dimensional model of the communicating vessels of an apparatus according to embodiments of the invention.

FIG. 6 shows a section of the three-dimensional model of the communicating vessels of an apparatus according to embodiments of the invention, indicating potential leaks of magnetic lines of force of the magnetic field.

FIG. 7 shows structural components of the apparatus forming the communicating vessels system and the hydraulic system of an apparatus according to embodiments of the invention.

FIG. 8 shows an axial section of the integrated dynamic core of the magnetic conductor indicating the direction of the propagation of magnetic lines of force matching the direction of movement of the monitored fluid.

FIG. 9 shows a three-dimensional model of the system of communicating vessels of the apparatus and the monitoring module.

Figure 10:
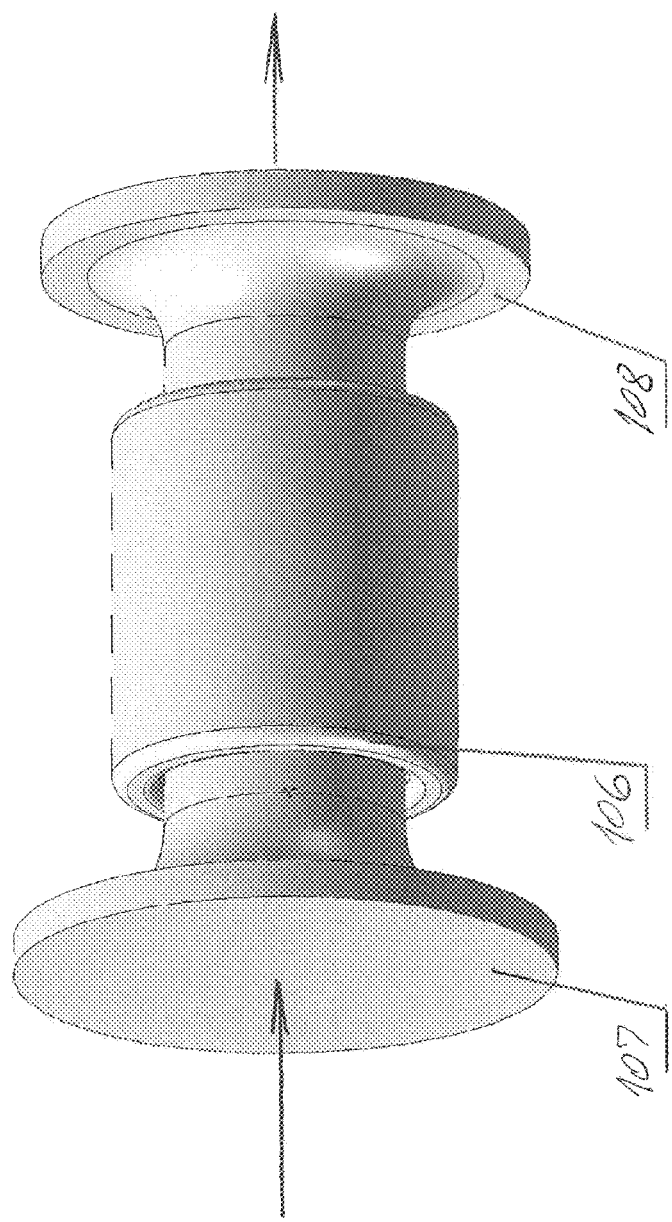
FIG. 10 is an example of a three-dimensional model of the core, which can function as an equivalent of a pulsed electromagnet, of a monitoring module of an apparatus according to embodiments of the invention.

FIG. 10 shows a three-dimensional model of the dynamic core.

Figure 11:
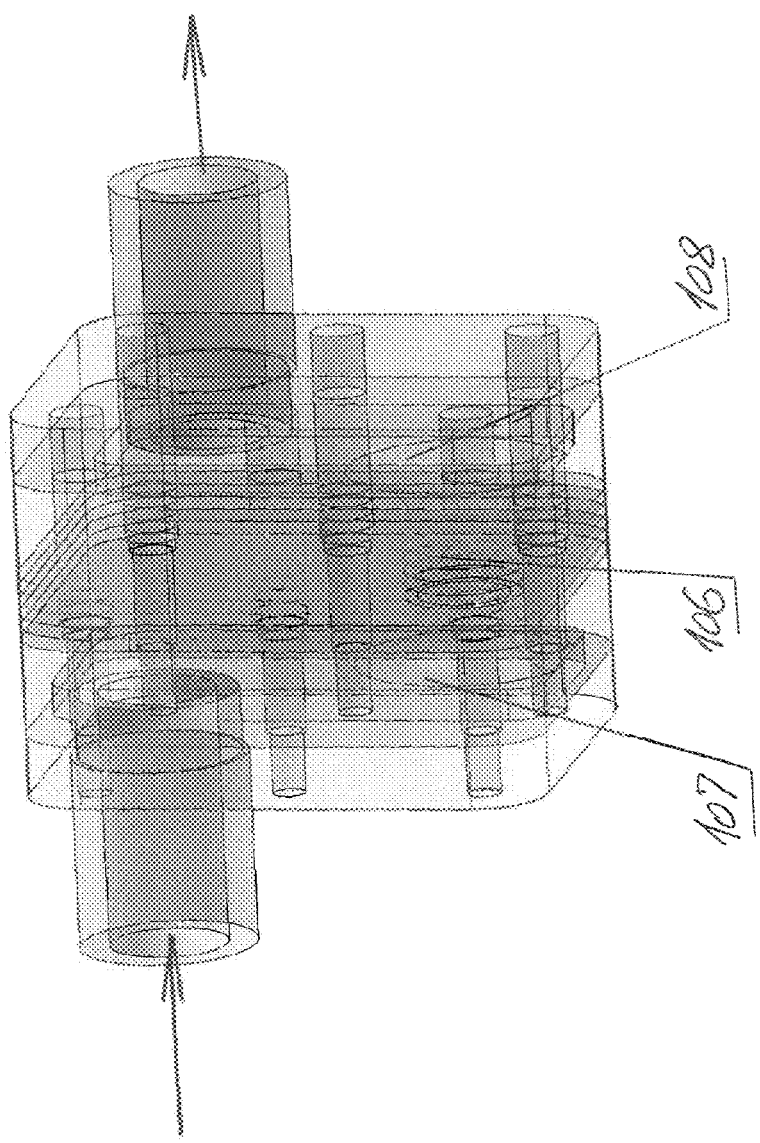
FIG. 11 is an example of a three-dimensional model of an apparatus according to embodiments of the invention.

FIG. 11 shows a three-dimensional model of the apparatus indicating the components of dynamic core and their interconnection with other components of the apparatus.

Figure 12:
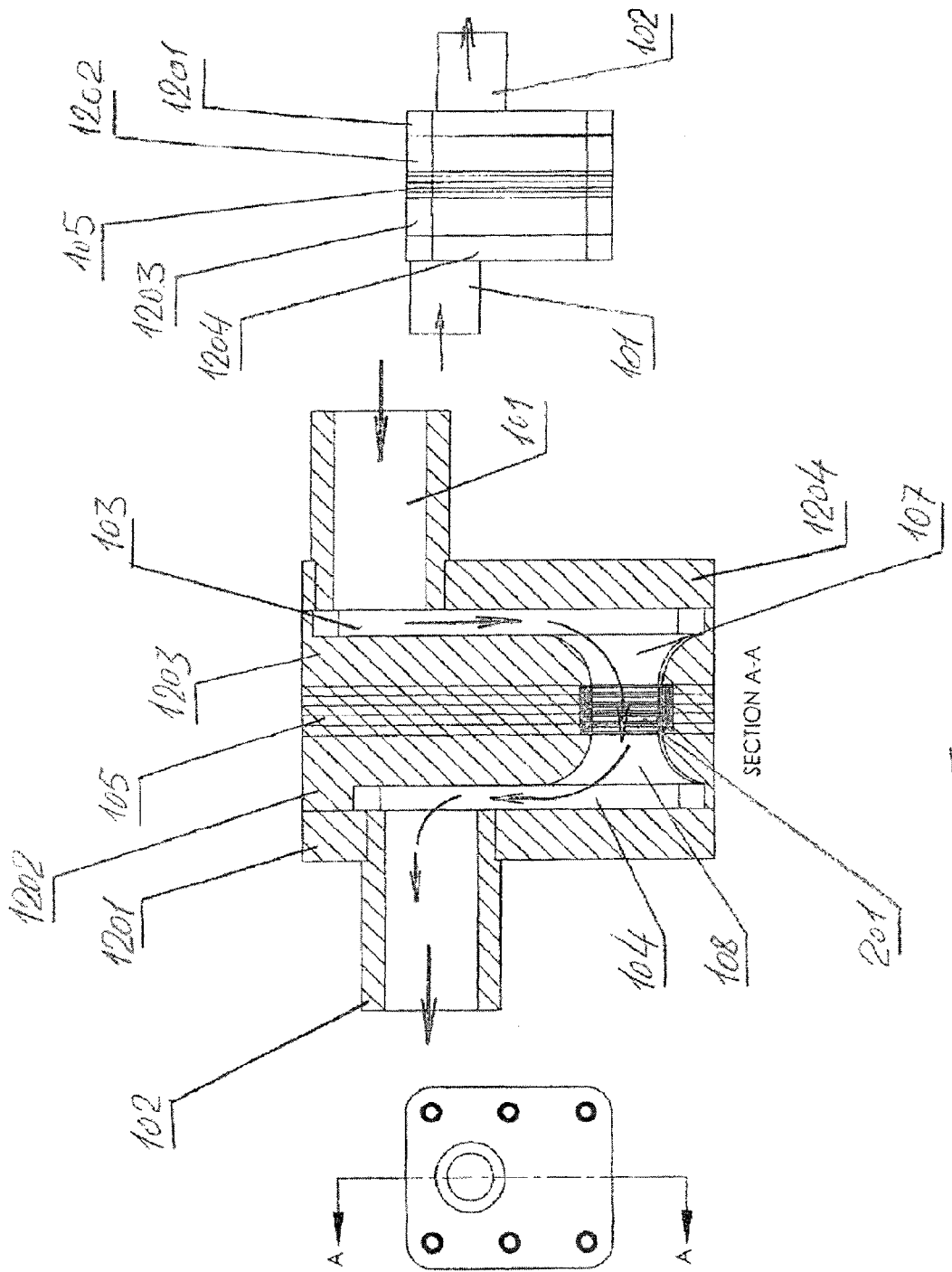
FIG. 12 is an example of an axial section of an apparatus according to embodiments of the invention.

FIG. 12 shows a longitudinal section of the apparatus identifying in detail various structural components forming the system of the communicating vessels and the dynamic core of the monitoring module magnetic conductor in them. The following reference numerals identify the following features:

1201—An external flange of the apparatus on the fluid outflow side.
1202—A structural component comprising a cavity in which the second vertical branch of the communicating vessels is formed, and conical reflector 108.
1203—A structural component comprising a cavity in which the first vertical branch of communicating vessels is formed, and conical reflector 107.
1204—The external flange of the apparatus on the fluid inflow side.

Figure 13:
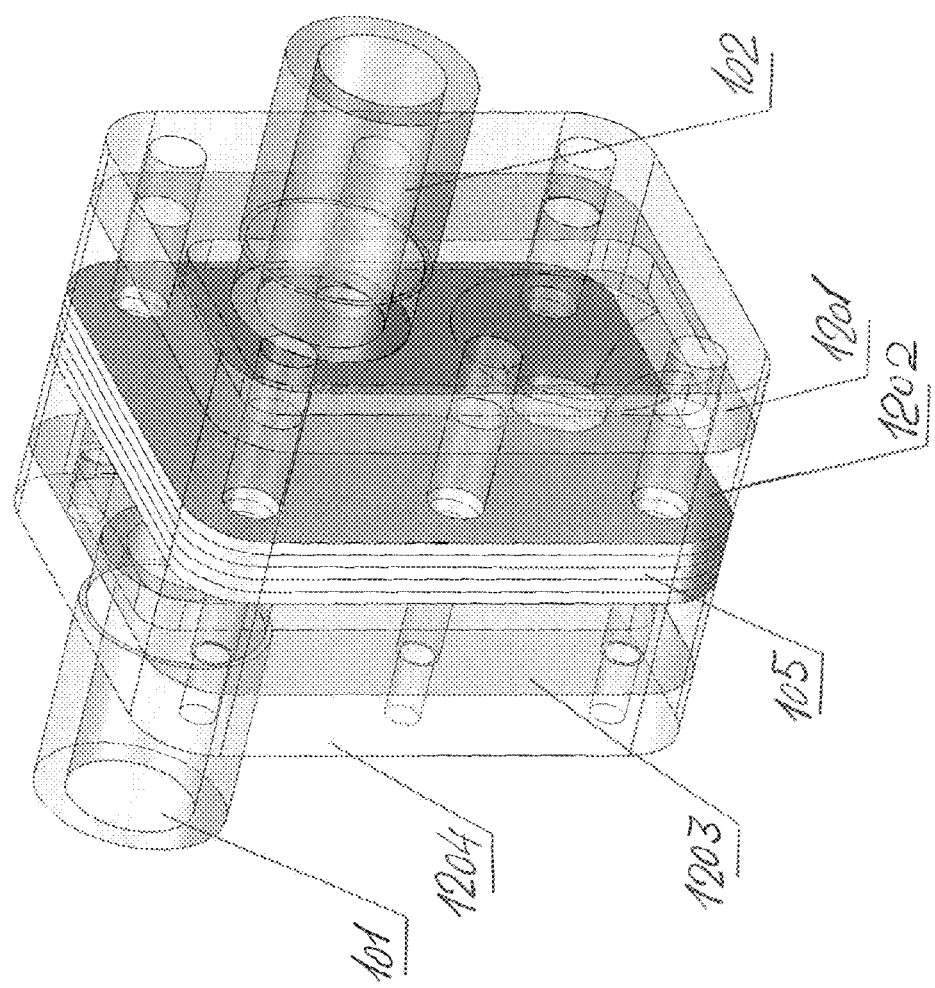
FIG. 13 is an example of a three-dimensional model of an apparatus according to embodiments of the invention.

FIG. 13 shows a three-dimensional model of an apparatus according to embodiments of the invention.

Figure 14:
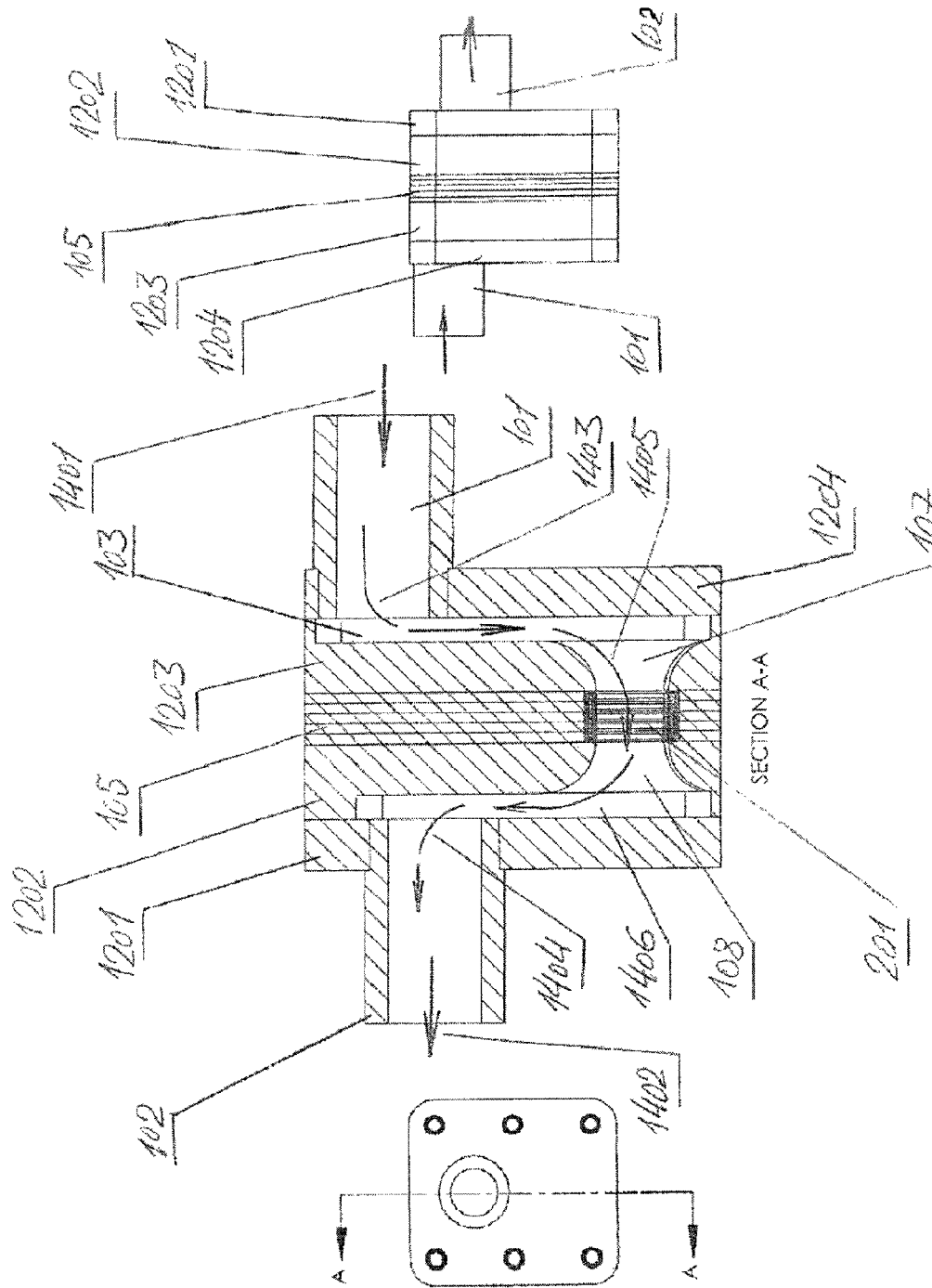
FIG. 14 is an example of a cross section of the apparatus with monitored fluid current parameters.

FIG. 14 shows trajectories of fluid movement in the apparatus, in longitudinal section view, similar to the longitudinal section view in FIG. 12. The following reference numerals identify the following features:

1401-Fluid flow at the apparatus inlet.
1402-Fluid flow at the apparatus outlet.
1403-Fluid flow bend at the first vertical branch inlet of the communicating vessels.

1404-Fluid flow bend at the second vertical branch outlet of the communicating vessels and at the apparatus outflow duct inlet.

Figure 15:
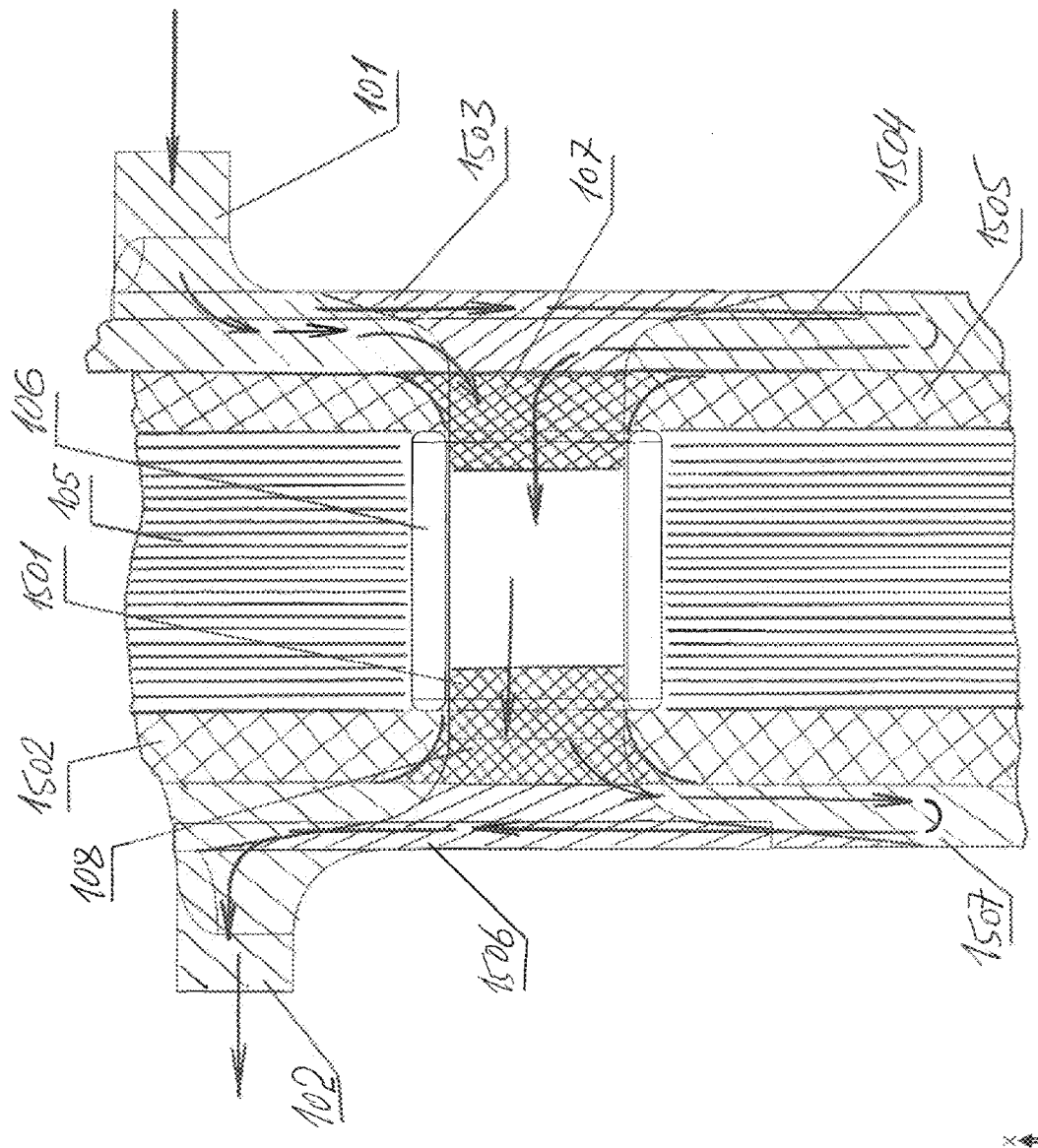
FIG. 15 is an example of a cross section of the monitoring module of an apparatus according to embodiments of the invention.

FIG. 15 shows a section of the monitoring module of an apparatus according to embodiments of the invention identifying various fluctuations of the monitored fluid flow in the communicating vessels. The following reference numerals identify the following features:

1501—A portion of the monitored fluid flow imitating passive part of the core.
1502—A polymer-based part.
1503—A vertical branch of the communicating vessels where fluid flows down.
1504—A vertical branch of the communicating vessels where fluid flows up.
1505—A polymer-based part.
1506—A vertical branch of the communicating vessels where fluid flows up.
1507—A vertical branch of the communicating vessels where fluid flows down.

Figure 16:
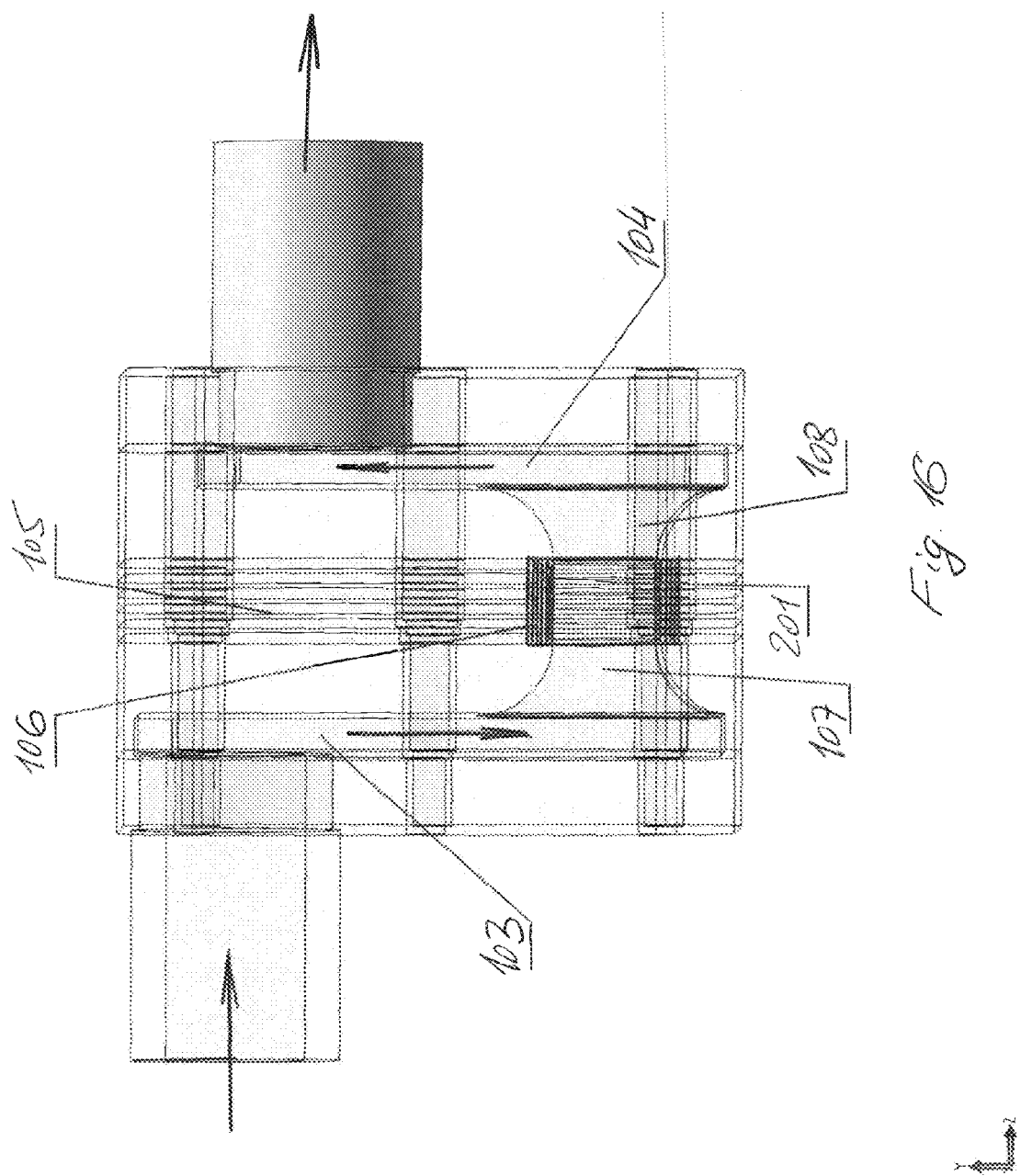
FIG. 16 is an example of a frontal projection of the apparatus with parts and components rendered semi-transparent and monitoring module core and solenoid identified.

FIG. 16 shows a flat model view of the apparatus, identifying various monitored fluid flow elements and their interaction with structural components of an apparatus according to embodiments of the invention.

Figure 17:
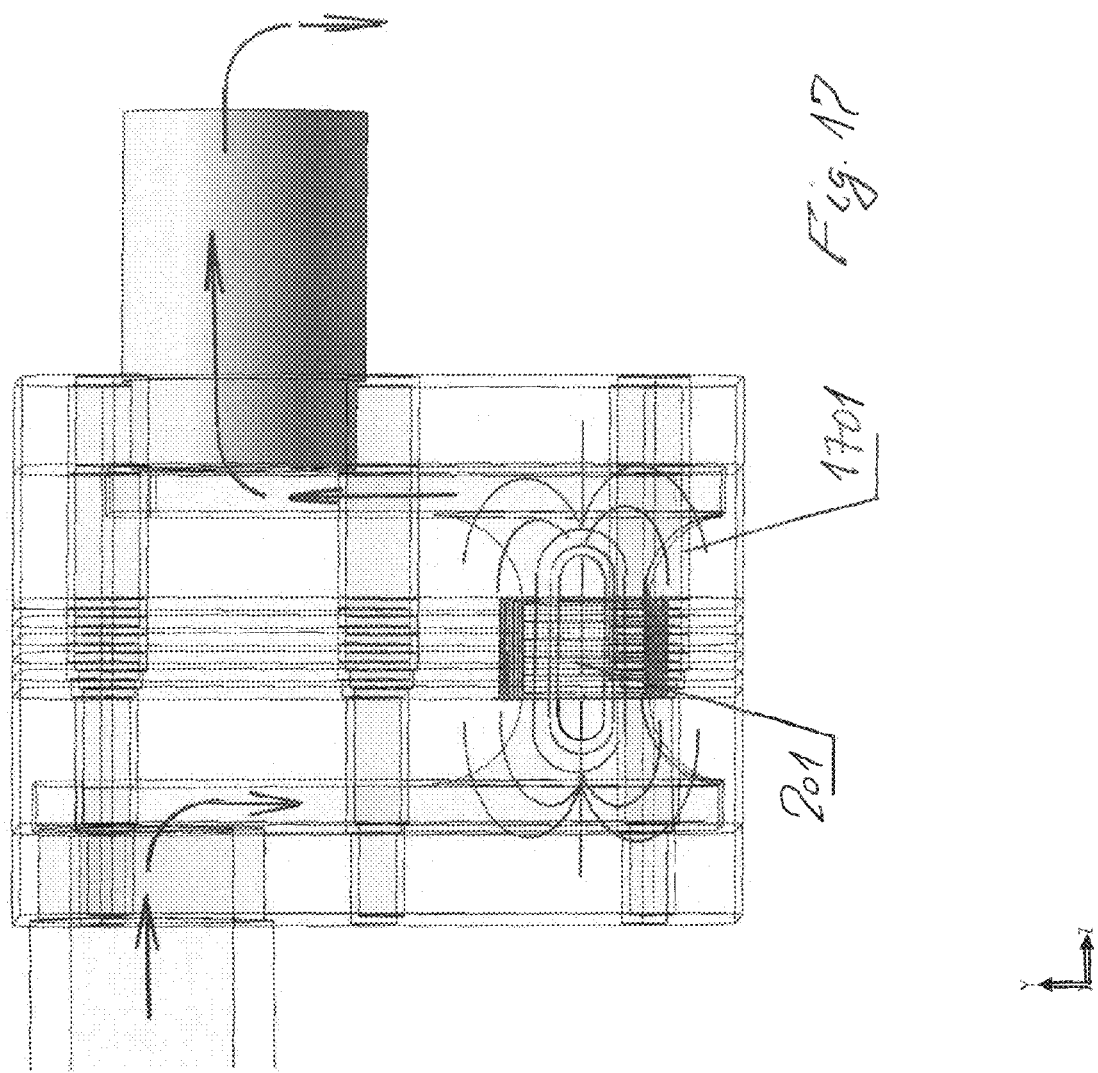
FIG. 17 shows an example of magnetic field magnetic lines of force in the frontal projection of an apparatus according to embodiments of the invention, with various details and components rendered semi-transparent.

FIG. 17 shows apparatus components and the monitored fluid in it, identifying magnetic lines of force of the field generated in the monitoring module. Number 1701 in the figure indicates the magnetic field in the monitoring module.

Figure 18:
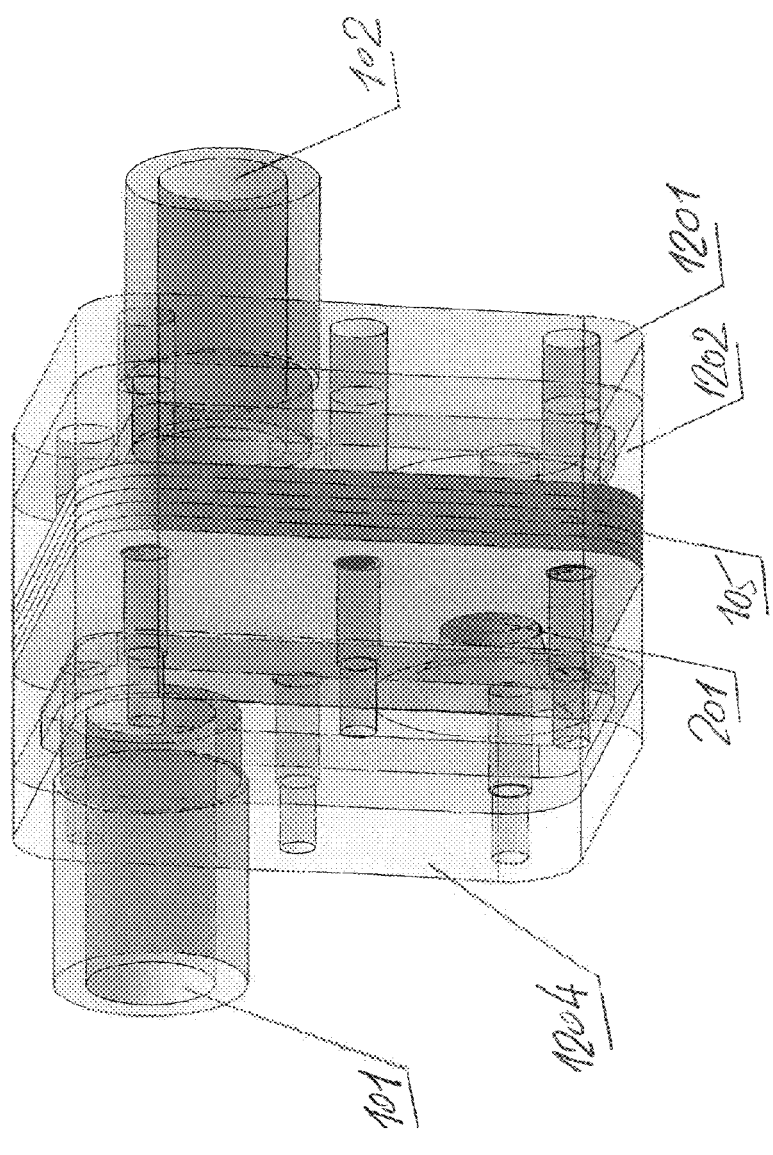
FIG. 18 is an example of a three-dimensional model of an apparatus according to one embodiment of the invention.

FIG. 18 shows a three-dimensional model of an apparatus according to embodiments of the invention viewed from the monitored fluid inflow side.

Figure 19:
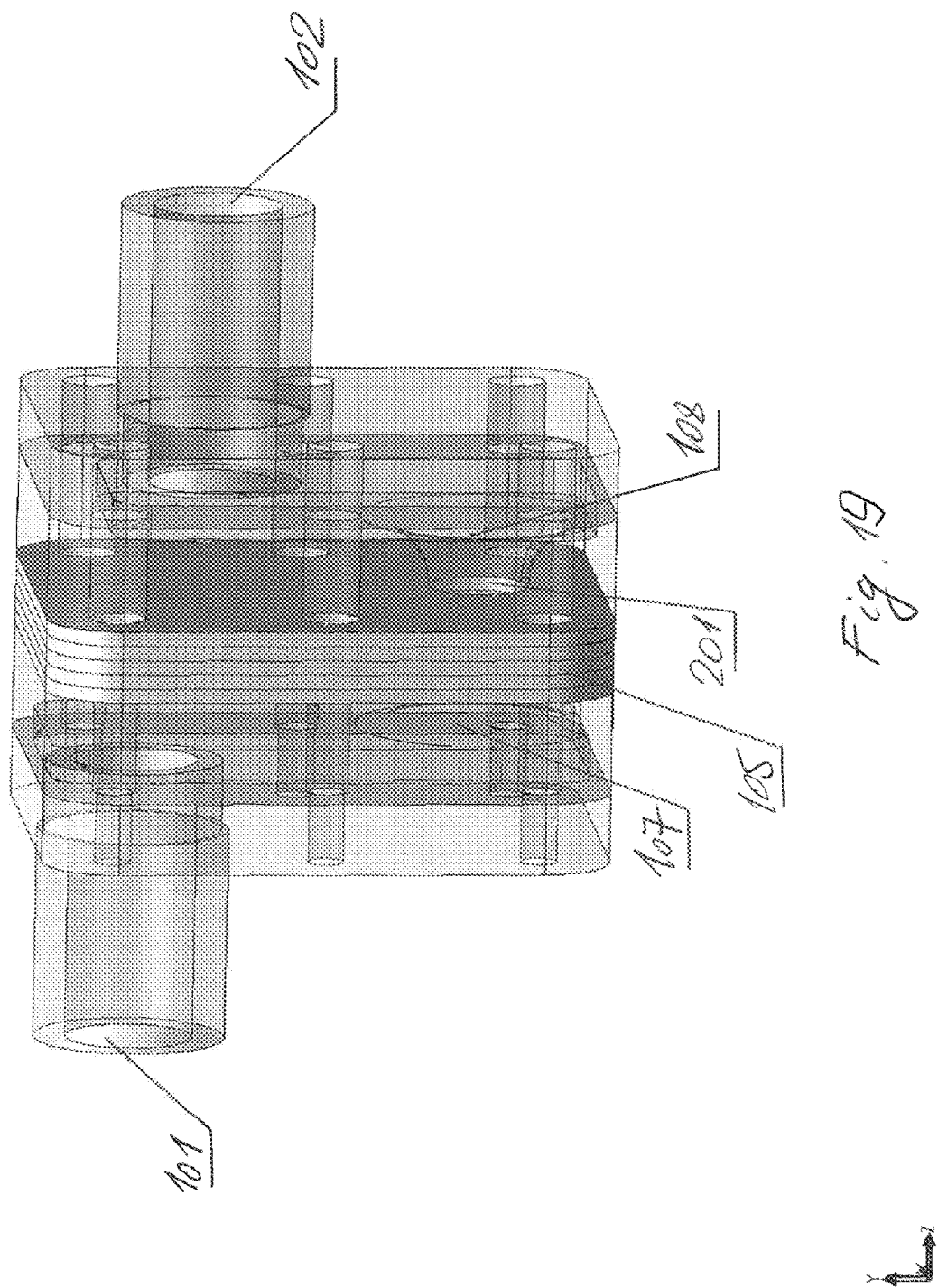
FIG. 19 is an example of a three-dimensional model of an apparatus according to one another embodiment of the invention.

FIG. 19 shows a three-dimensional model of an apparatus according to embodiments of the invention viewed from the monitored fluid outflow side.

Figure 20:
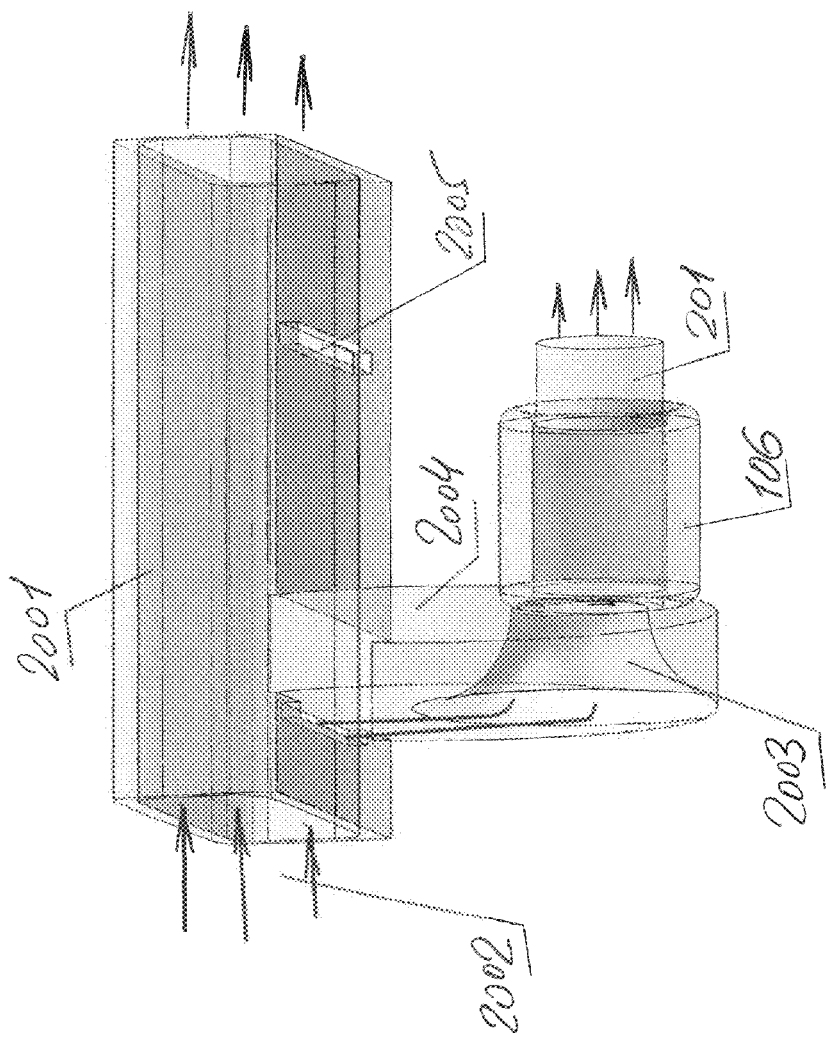
FIG. 20 is an example of a model of monitored fluid flow isolated from the primary fluid flow passing in the primary pipeline; one conical reflector at monitoring module inlet is shown.

FIG. 20 shows monitored fluid flow model when only some of the fluid flow is isolated for monitoring purposes; one reflector is shown. The following reference numerals identify the following features:

2001—A primary fluid flow.
2002—A primary fluid flow direction.
2003—A first vertical branch of the communicating vessels.
2004—An apparatus structure.
2005—An opening for removing monitored fluid and injecting it into the primary fluid flow.

Figure 21:
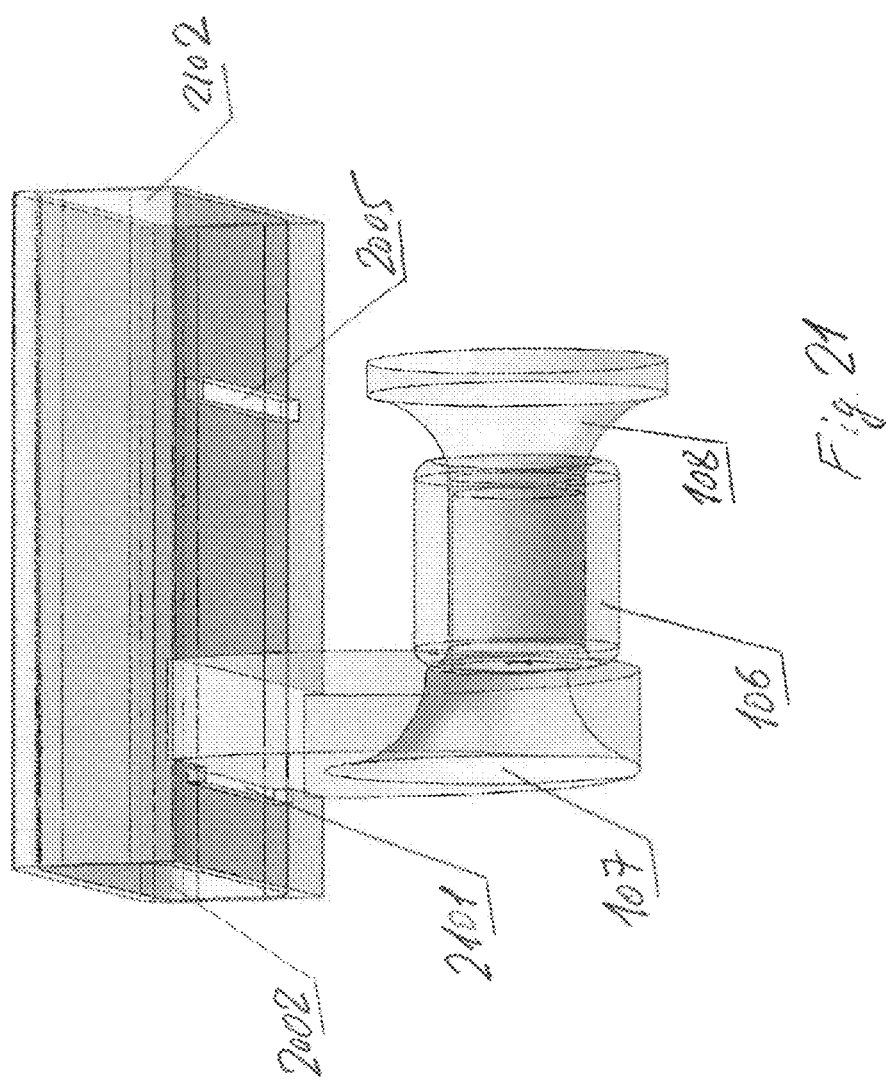
FIG. 21 is an example of a model of monitored fluid flow isolated from the primary fluid flow passing in the primary pipeline; two conical reflectors are shown, one at the monitoring module inlet and another at the monitoring module outlet.

FIG. 21 shows a monitored fluid flow model when only a portion of the fluid flow is isolated for monitoring purposes; two reflectors are shown. The following reference numerals identify the following features:

2101—An opening for a portion of fluid flow to be transferred to monitoring.
2102—A pipeline for primary fluid flow.

Figure 22:
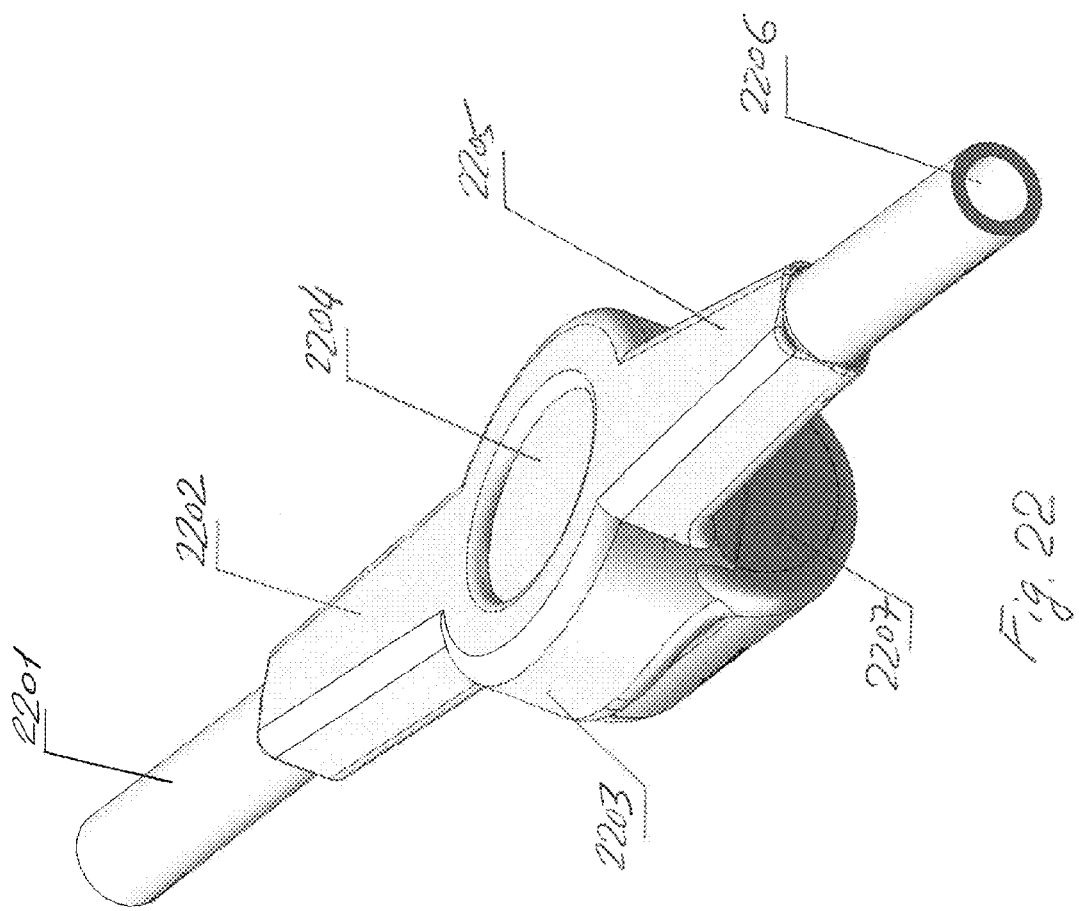
FIG. 22 is an example of a three-dimensional module of the fluid flow rate counter with a built-in apparatus according to embodiments of the invention for monitoring fluid component concentration.

FIG. 22 shows an apparatus application case for an apparatus built into a fluid flow rate counter. The following reference numerals identify the following features:

2201—A pipeline for supplying the fluid to the fluid flow rate counter.
2202—A primary fluid flow pipeline.
2203—A fluid flow rate counter body comprising the flow rate control mechanism.
2204—A fluid flow rate indicator opening.
2205—A continuation of the primary fluid flow pipeline.
2206—A pipeline for primary liquid flow discharge from the counter.
2207—A dynamic monitoring apparatus.

Figure 23:
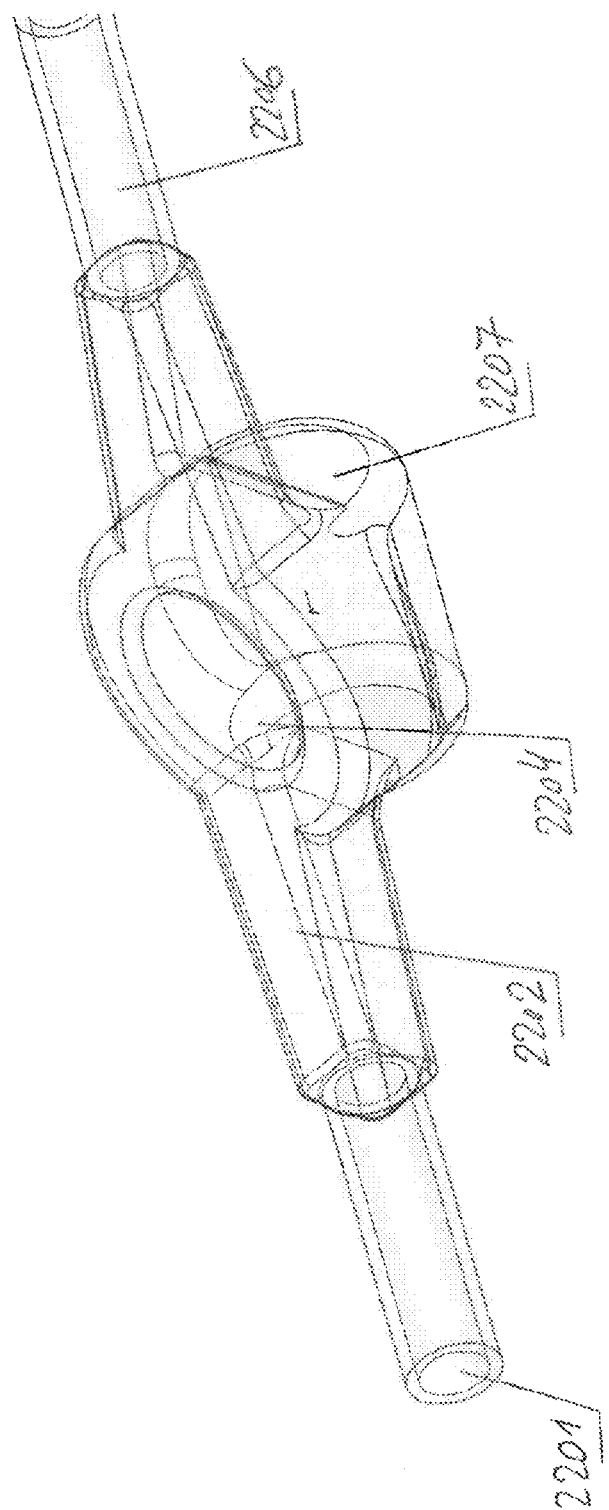
FIG. 23 is an example of a three-dimensional model of the fluid flow rate counter with a built-in apparatus according to embodiments of the invention for monitoring fluid component concentration with various components and parts rendered semi-transparent.

FIG. 23 shows a fluid flow rate counter with a built-in apparatus for dynamic control with the structure of an apparatus according to embodiments of the invention rendered semi-transparent in the figure.

FIG. 24 shows a fluid flow rate counter with an apparatus according to embodiments of the invention built in, viewed from the apparatus side.

Test Results

Characteristic and most complex monitoring cases of fluid material state parameters were selected for qualification tests; the tests demonstrated that results are visible by contrast against the general background giving a full understanding of the nature and dimensions of the parameters of material objects and their components.

Test results showed that in the apparatus, each solenoid having its own set of technical characteristics, also has a constant coefficient which describes the correlation between the absolute value of the parameter corresponding to 1 millivolt of the amplitude of the measured parameter to the absolute value of this parameter.

This constant coefficient makes it possible to selectively choose only the indicators corresponding to the coefficient, with the coefficient making it possible to operate the apparatus in the standalone automatic mode.

Analysis of the Test Results

Qualification test result analysis showed that the embodiments of the invention achieve the objective of ensuring remote, non-contact monitoring of the parameters of the state of any material object with precision exceeding that of various known monitoring techniques. Advantageously, embodiments of the invention allow performing active dynamic monitoring or tracking of fluid parameters in real time, without interrupting the fluid flow.

Examples of Applications

In some embodiments, a device for magnetic resonance water or water solution quality control includes a segment of a pipeline with a circular sensor installed on the pipe's external surface connected to a power supply source and a signal control, amplification and identification system. The system includes customizable transmission device used to transmit amplified and identified signals to operator control panel or to a cell phone.

In some embodiments, water quality may be measured in agricultural water streams using non-contact resonance monitoring, as described herein.

In some embodiments, water, fluid, and water solution acidity may be measured. The water and water solution acidity level of the non-contact resonance monitoring range may be essentially unlimited. Monitoring precision can be adjusted as needed, but shall not be less than about 0.1 of acidity monitoring unit adopted in accordance with relevant standards. Monitoring precision does not depend on organic matter concentration in water or in water solution, and does not depend on the level of water solution aggressiveness since all monitoring operations are performed remotely, without any contact with the monitored fluid.

In some embodiments, nutrient concentration in water solution for plant watering in the agricultural section may be performed. If substances to be injected in a nutrient solution are known in advance, the integrated sensor can include a number of selective sensors corresponding to the number of the components in the solution. Each sensor may be set up for one component. The measurement precision is within about 0.5 milligrams per liter.

In some embodiments, water solution conductivity may be measured. It will be appreciated that acidity level monitoring is similar to acidity monitoring. The measurement precision may be within about 1 Microsiemens.

In some embodiments, integrated quality control of fluids, water, and water solutions may be performed. Examples of two approaches include: 1) using one sensor to indicate a combined water or fluid quality parameter; and 2) using number of sensors corresponding to the number of monitoring parameters or materials to be monitored, each sensor monitoring the state of just one material or its concentration.

In some embodiments, heavy metal concentrations in fluids, water, and water solutions may be monitored. The monitoring can be performed integrally; in which case the sensor indicates the presence of all the metals in the water or water solution. The monitoring can be performed selectively; in which case sensors set to monitor the concentration of each metal individually must be included in the integrated sensor module. The sensor module can include sensors for combined integrated monitoring of the state and quality of the water or water solution including simultaneous monitoring of all water or water solution quality parameters.

In some embodiments, organic matter levels or concentrations in fluids, water, and water solutions may be monitored. The organic matter concentration can be monitored integrally, for example, bw monitoring the general concentration of all organic matter and compounds in water or water solution. Organic matter concentration monitoring can be selective; in which case the integrated sensor module must include selective sensors set to individual organic components. Methods of monitoring biological components in water or water solutions can preclude the distortion of results due to complete absence of contact in the measurement process.

In some embodiments, water ad water solution temperatures may be monitored. The water solution temperature monitoring may be conducted similarly to conductivity monitoring.

In some embodiments, the permittivity of fluids, water, and water solutions may be monitored. Monitoring permittivity is performed similarly to monitoring organic matter level or concentration in water or water solutions. The monitoring may be performed by specially selected sensors or groups of sensors are installed on the external diameter of the pipeline or supplied with the segment of the pipeline built into the existing pipeline. Software as part of the technology implemented through apparatus application identifies sensor signals in order to interpret the concentration of monitored parameter in the water or water solution.

In some embodiments, non-contact inspection of drinking water compliance with standards may be performed. Examples of two versions of the monitoring devices include a first version is for installation directly on the pipeline before the faucet, in households; a second version may be portable, for placing water samples from the faucet in the segment of the pipeline on which the sensor is installed. Both versions may be made from plastic, e.g., polyvinyl chloride, are small and easy to use.

An operating principle of the monitoring devices is comparing resonance sensor reference signals with the signal obtained from sample measurement; the reference signal is obtained using water in full compliance with standards; device sensor registers the slightest deviations from the reference signal; sensitivity threshold is about 0.000000005 gram for metals; about 0.000000000001 gram for radioactive isotopes; about 0.000001 grams for scale-forming salts and silicates; about 0.0000001 grams for organic acids and compounds, including phenols and traces of surfactants, cleaning agents and mineral fertilizers; all concentrations above are per one liter of water.

The monitoring device may not separate or register selectively every component of contamination or admixtures, but its sensitivity allows it to determine 50% threshold of potable water contamination concentration hazardous to health; the high precision of a household item makes it possible to continuously monitor the quality of water used for household purposes, and to take measures to remove contamination even before contamination concentration reaches dangerous levels. Many developed countries' public health standards recommend continuous monitoring of water quality, which may be hard to satisfy in absence of a reliable, simple to use and accurate device on the market, at a price allowing for large-scale demand and use. Embodiments of the invention allow these standards to be met, both those related to the safety of materials used, and to their application. The monitoring apparatus are easy to manufacture, do not require unconventional manufacturing technologies and can be produced in small facilities. As such, the apparatus can be produced using the so-called "zoning" method, i.e., assembly in places of sale, thus lowering transportation costs and allowing for just-in-time inventory system avoiding warehouse expenses.

In some embodiments, acidity and alkalinity levels in fluids, water, and water solutions for household needs may be monitored. This application may be carried in a fashion similar to the applications presented above. The monitoring may be performed in conjunction with cleaning supplies, personal hygiene products, cosmetics, etc. The application includes monitoring acidity or alkalinity levels in water using one scale and for general water analysis using a different scale.

In some embodiments, heavy metal concentrations in fluids, water, and water solutions may be monitored.

It will be appreciated that the monitoring disclosed herein may be performed by various entities, including corporations, real-estate owners such as office buildings or large residential buildings. For example, the monitoring may take the form of continuous water monitoring in central conditioning systems.

Various embodiments of the invention allow one or more of the following advantages:

Monitoring may be carried out 24 hours a day in real time;

Monitoring may be carried out automatically; the monitoring process does not require operator participation;

Monitoring results may be transmitted to the maintenance department in real time thus preventing accidents since decisions can be made as soon as measurement results are obtained;

Monitoring results may not be affected by organic substance concentration increases and decreases in the monitored fluids, e.g., in water;

Since monitoring is carried out without direct contact with monitored fluid, water solution or water, problems related to corrosion or any other destructive factor do not arise;

The system does not require consumables, in contrast to existing monitoring systems, thereby reducing operating costs; and The monitoring system operates in standalone automatic mode and does not require regular maintenance.

It will be appreciated by those skilled in the art that various omissions, additions and modifications may be made to the methods and structures described above without departing from the scope of the invention. All such modifications and changes are intended to fall within the scope of the invention, as defined by the appended claims.

What is claimed is:

1. An apparatus for fluid content monitoring, the apparatus comprising:
a monitoring module connected to:
a first system for monitored fluid flow turbulence level transformation and transformed fluid flow into the monitoring module; and
a second system for fluid flow turbulence level restoration and fluid outflow from the monitoring module,
wherein a monitored fluid flow is monitored by a RLC circuit feed element of the monitoring module, the RLC circuit feed element comprising a core with a pulsed electrical magnet,
wherein the first system comprises an inlet conical reflector comprising a peak pointing toward an inlet of the monitoring module, the inlet conical reflector disposed coaxially to the RLC circuit feed element of the monitoring module.

2. The apparatus of claim 1, further comprising:
a first vessel for fluid flow, the first vessel comprising the first system;
a second vessel for fluid flow, the second vessel comprising the second system; and
a third vessel for fluid flow, the third vessel comprising a monitoring module hydraulic system,
wherein the first, second, and third vessels are in fluid communication.

3. The apparatus of claim 1, further comprising:
a first vessel for fluid flow, the first vessel comprising the first system;
a horizontal component comprising a monitoring module hydraulic system; and
a second vessel for fluid flow, the second vessel comprising the second system, wherein the first vessel comprises a vertical component, wherein the second vessel comprises a vertical component, and wherein the horizontal component connects the first vessel to the second vessel.

4. The apparatus of claim 3, wherein the horizontal component comprises at least one cylindrically shaped duct.

5. The apparatus of claim 3, wherein the RLC circuit feed element is installed coaxially to the horizontal component of the communicating vessels.

6. The apparatus of claim 1, wherein the feed element is a solenoid connected to power supply and control systems.

7. The apparatus of claim 1, wherein the second system comprises an outlet conical reflector comprising a peak pointing toward an outlet of the monitoring module, the outlet conical reflector disposed coaxially to the RLC circuit feed element of the monitoring module.

8. The apparatus of claim 1, further comprising:
an outlet conical reflector comprising cone peak pointing toward an outlet of the monitoring module, the reflector disposed coaxially to the RLC circuit feed element of the monitoring module; and
a horizontal component connecting a first vessel comprising the first system to a second vessel comprising the second system, the horizontal component disposed in the RLC circuit feed element of the monitoring module,
wherein the inlet conical reflector, outlet conical reflector, and horizontal component comprise components forming the dynamic core of a pulsed electromagnet.

9. The apparatus of claim 8, wherein the first vessel, second vessel, and a hydraulic system of at least the monitoring module are in fluid communication via two vertical components and one horizontal component connecting the first vessel to the second vessel, the horizontal component comprising:
at least one cylindrically shaped duct, and;
at least one solenoid disposed coaxially to the duct, the solenoid comprising the RLC circuit feed element of the monitoring module.

10. An apparatus for fluid content monitoring, the apparatus comprising:
a monitoring module connected to:
a first system for monitored fluid flow turbulence level transformation and transformed fluid flow into the monitoring module; and
a second system for fluid flow turbulence level restoration and fluid outflow from the monitoring module,
wherein a monitored fluid flow is monitored by a RLC circuit feed element of the monitoring module, the RLC circuit feed element comprising a core with a pulsed electrical magnet,
wherein the second system comprises an outlet conical reflector comprising a peak pointing toward an outlet of the monitoring module, the outlet conical reflector disposed coaxially to the RLC circuit feed element of the monitoring module.

* * * * *